US 6,676,610 B2

(12) United States Patent
Morton et al.

(10) Patent No.: US 6,676,610 B2
(45) Date of Patent: Jan. 13, 2004

(54) DISPOSABLE PATIENT INTERFACE FOR INTRADUCTAL FLUID ASPIRATION SYSTEM

(75) Inventors: Kevin B. Morton, Mission Viejo, CA (US); Rex O. Bare, Lake Forest, CA (US); Jeffrey C. Smith, Newport Beach, CA (US); Timothy J. Payne, Santa Ana, CA (US); Paul Gleason, Laguna Niguel, CA (US)

(73) Assignee: Neomatrix, LLC, Irvine, CA (US)

( * ) Notice: Subject to any disclaimer, the term of this patent is extended or adjusted under 35 U.S.C. 154(b) by 0 days.

(21) Appl. No.: 10/072,546

(22) Filed: Feb. 8, 2002

(65) Prior Publication Data

US 2002/0183719 A1 Dec. 5, 2002

Related U.S. Application Data

(63) Continuation-in-part of application No. 09/870,402, filed on May 30, 2001.

(51) Int. Cl.$^7$ .................................................. A61B 5/00
(52) U.S. Cl. ........................ 600/573; 604/74; 604/317
(58) Field of Search ................................ 600/573, 574, 600/38; 604/119

(56) References Cited

U.S. PATENT DOCUMENTS

| | | | |
|---|---|---|---|
| 3,608,540 A | * | 9/1971 | Sartorius |
| 3,786,801 A | * | 1/1974 | Sartorius |
| 3,822,703 A | * | 7/1974 | Davisson |
| 4,249,481 A | * | 2/1981 | Adams |
| 4,393,811 A | * | 7/1983 | Bodmin |
| 4,452,779 A | * | 6/1984 | Cockerill |
| 4,542,750 A | * | 9/1985 | Ettare |
| 4,680,028 A | * | 7/1987 | Stuart |
| 4,761,160 A | * | 8/1988 | Vermillion |
| 4,794,915 A | | 1/1989 | Larsson .................. 601/153 |
| 4,883,464 A | * | 11/1989 | Morifuki |
| 4,941,433 A | * | 7/1990 | Hanauer |
| 4,964,851 A | * | 10/1990 | Larsson |
| 5,007,899 A | * | 4/1991 | Larsson |
| 5,049,126 A | * | 9/1991 | Larsson |
| 5,476,492 A | * | 12/1995 | Unrug |
| 5,482,004 A | * | 1/1996 | Chowdhury |
| 5,493,995 A | * | 2/1996 | Chowdhury |
| 5,576,329 A | | 11/1996 | Hennessey |

(List continued on next page.)

FOREIGN PATENT DOCUMENTS

| | | |
|---|---|---|
| WO | WO 98/22160 | 5/1998 |
| WO | WO00/39557 | 7/2000 |
| WO | WO00/42841 | 7/2000 |
| WO | WO00/43038 | 7/2000 |
| WO | WO00/43553 | 7/2000 |
| WO | WO00/70349 | 11/2000 |
| WO | WO00/72766 | 12/2000 |
| WO | WO02/38032 | 5/2002 |

OTHER PUBLICATIONS

International Search Report for PCT Application PCT/US02/16900 Filed May 29, 2002.
Petro et al., *Nature*, 1981, 290, 201–208.

(List continued on next page.)

*Primary Examiner*—Charles Marmor
(74) *Attorney, Agent, or Firm*—Knobbe, Martens, Olson & Bear, LLP

(57) ABSTRACT

Disclosed is a disposable patient interface for an intraductal fluid aspiration system. The interface has a flexible tubular distal member for contacting the patient, and a rigid proximal member forming a vacuum chamber therein. The rigid member has a vacuum aperture for communication with a source of vacuum. The flexible member preferably has a low modulus of elasticity and a high tear strength, such that it can be stretched to fit over a rigid support without rupture.

17 Claims, 14 Drawing Sheets

U.S. PATENT DOCUMENTS

| | | | |
|---|---|---|---|
| 5,627,034 A | 5/1997 | Gould et al. | |
| 5,645,537 A | 7/1997 | Powles et al. | |
| 5,664,984 A | 9/1997 | Laughridge | |
| 5,720,722 A | 2/1998 | Lockridge | |
| 5,741,649 A | 4/1998 | Inazawa | |
| 5,776,098 A | 7/1998 | Silver et al. | |
| 5,776,177 A | 7/1998 | MacWhinnie et al. | |
| 5,797,875 A | 8/1998 | Silver | |
| 5,798,266 A | 8/1998 | Quay et al. | |
| 5,810,772 A | 9/1998 | Nieberger | 604/74 |
| 5,810,796 A | 9/1998 | Kimura et al. | |
| 5,846,739 A | 12/1998 | Gould et al. | |
| 5,855,889 A | 1/1999 | Watson et al. | |
| 5,885,246 A | 3/1999 | Ford | |
| 5,895,640 A | 4/1999 | Khalkhali | |
| 5,902,267 A | 5/1999 | Medo | |
| 5,902,279 A | 5/1999 | Powles et al. | |
| 5,902,293 A | 5/1999 | Liu | 604/313 |
| 5,913,686 A | 6/1999 | Van Winkle | |
| 5,914,238 A | 6/1999 | Keesee et al. | |
| 5,922,836 A | 7/1999 | Watson et al. | |
| 5,941,847 A | 8/1999 | Huber et al. | |
| 6,004,186 A | 12/1999 | Penny | |
| 6,004,756 A | 12/1999 | Watson et al. | |
| 6,063,029 A | 5/2000 | Saita et al. | |
| 6,110,140 A | 8/2000 | Silver | |
| 6,168,779 B1 | 1/2001 | Barsky et al. | 424/9.2 |
| 6,221,622 B1 | 4/2001 | Love | 437/7.23 |
| 6,287,521 B1 | 9/2001 | Quay et al. | |
| 6,314,315 B1 | 11/2001 | Hung et al. | 600/547 |
| 6,316,189 B1 | 11/2001 | Haddad et al. | |
| 6,316,215 B1 | 11/2001 | Adair et al. | |
| 6,328,709 B1 | 12/2001 | Hung et al. | 604/74 |
| 6,358,226 B1 | 3/2002 | Ryan | 604/74 |
| 6,379,327 B2 | 4/2002 | Lundy | 604/74 |
| 6,383,163 B1 | 5/2002 | Kelly et al. | 604/74 |
| 6,383,164 B1 | 5/2002 | Johansen et al. | 604/74 |
| 6,387,072 B1 | 5/2002 | Larsson et al. | 604/74 |
| 6,391,026 B1 | 5/2002 | Hung et al. | 606/41 |
| 6,398,765 B1 | 6/2002 | Hung | 604/284 |
| 6,413,228 B1 | 7/2002 | Hung et al. | 600/562 |
| 6,471,660 B1 | 10/2002 | Covington | |
| 6,517,513 B1 | 2/2003 | Covington et al. | 604/74 |
| 2001/0001059 A1 | 5/2001 | Love | 435/7.1 |
| 2001/0034038 A1 * | 10/2001 | Hung | |
| 2001/0039015 A1 * | 11/2001 | Sauter | |
| 2001/0047148 A1 | 11/2001 | Suh | 604/74 |
| 2002/0002343 A1 * | 1/2002 | Hung et al. | |
| 2002/0007115 A1 * | 1/2002 | Hung et al. | |
| 2002/0010405 A1 * | 1/2002 | Hung et al. | |
| 2002/0013539 A1 * | 1/2002 | Hung | |
| 2002/0019017 A1 | 2/2002 | Love et al. | 435/7.23 |
| 2002/0037265 A1 | 3/2002 | Hung et al. | 424/70.1 |
| 2002/0045162 A1 | 4/2002 | Hung | 435/5 |
| 2002/0058887 A1 | 5/2002 | Soito et al. | 600/573 |
| 2002/0062103 A1 | 5/2002 | Larsson et al. | 604/74 |
| 2002/0072702 A1 | 6/2002 | Quay | 604/74 |
| 2002/0086341 A1 | 7/2002 | Nguyen | 435/7.23 |

OTHER PUBLICATIONS

Adami et al., "Absence of association between reproductive variables and the risk of breast cancer in young women in Sweden and Norway," *British Journal of Cancer*, vol. 62, pp. 122–126 1990.

America Cancer Society *Cancer facts and figures*, 1996.

American Cancer Society *Breast cancer facts and figures*, 1996.

Anderson et al., *Cancer*, vol. 65, 1901–1908 1989.

Basu et al., "Serum vitamins A and E, beta–carotene, and selenium in patients with breast cancer," *Journal of the American College of Nutrition*, vol. 8, pp. 524–529 1989.

Bendich et al., "Antioxidant nutrients and immune function," *Advances in Experimental Medicine and Biology*, vol. 262, New York: Plenum Press 1990.

Brisson et al., "Diet, mammographic features of breast tissue, and breast cancer risk," *American Journal of Epidemiology*, vol. 130, pp. 14–24 1989.

Britton et al., *Carotenoids vol. 1a: Isolation and analysis*. Basel: Birkhausen Verlag 1995.

Burton et al., "Antioxidant action of carotenoids," *Journal of Nutrition*, vol. 119, pp. 109–115 1989.

Burton et al., "Beta–carotene: An unusual type of lipid antioxidant," *Science*, vol. 224, pp. 569 1984.

Byers et al., "Dietary carotenes, vitamin C, and vitamin E as protective antioxidants in human cancers," *Annual Review of Nutrition*, vol. 12, pp. 139–159 1992.

Byers et al., "Lactation and breast cancer," *American Journal of Epidemiology*, vol. 121, pp. 139–159 1985.

Dawood et al., *American Journal of Obstetrics and Gynecology*, 138, 20–24, 1980.

DeLuca, "Vitamin A" In: *The fat–soluble vitamins*, H. Deluca (Ed.), pp. 1–67, New York; Plenum Press. 1978.

Di Mascio et al., "Antioxidant defense systems: The role of carotenoids, tocopherols, and thiols," *American Journal of Clinical Nutrition*, vol. 53, pp. 194–200 1991.

Ewertz et al., "Dietary factors and breast–cancer risk in Denmark," *International Journal of Cancer*, vol. 46, pp. 779–784 1990.

Gaitan et al., *Endocrinology*, Sep, S1(3), 515–520, 1967.

Greiner *Pharmaceutical Tech.*, May 1993, pp. 28–44 1993.

Haagensen et al., *Breast carcinoma: Risk and detection*, Philadelphia: W.B. Saunders Company 1981.

Hill et al., "Retinoids and Cancer Prevention," *Annu. Rev. Nutr.* vol. 12, pp. 161–181 1992.

Hislop et al., "Diet and histologic types of benign breast disease defined by subsequent risk of breast cancer," *American Journal of Epidemiology*, vol. 131, pp. 263–270 1990.

Holmes et al., "Dietary guidelines," In: *Reducing breast cancer in women*, B. Stoll (Ed.), pp. 135–144 1995.

Inaji et al., *Cancer* vol. 60, 3008–3013 1987.

Ing et al., "Unilateral breast feeding and breast cancer," *The Lancet*, vol. 7, pp. 124–127 1977.

Katsouyanni et al., "Risk of breast cancer among Greek women in relation to nutrition intake," *Cancer*, vol. 61, pp. 181–185 1988.

Kinsel et al., *Cancer Res.* 49: 1052–1056, 1989.

Knecht et al., "Serum vitamin A and subsequent risk of cancer: Cancer incidence follow–up of the finish mobile clinic health examination survey," *American Journal of Epidemiology*, vol. 132, pp. 857–870 1990.

Krinsky et al., "Interaction of oxygen and oxy–radicals with carotenoids," *Journal of the National Cancer Institute*, vol. 69, pp. 205 1982.

Krinsky, "Actions of Carotenoids in Biological Systems," *Annu. Rev. Nutr*, vol. 13, pp. 561–587 1993.

Kvale et al., "Lactation and cancer risk: Is there a relationship specific to breast cancer," *Journal of Epidemiology and Community Health*, vol. 42, pp. 30–37 1987.

Layde et al., "The independent association of parity, age at first full–term pregnancy, and duration of breastfeeding with the risk of breast cancer," *Journal of Clinical Epidemiology*, vol. 42, pp. 963–973 1988.

Levin et al., "Lactation and menstrual function as related to cancer of the breast," *American Journal of Public Health*, vol. 54, pp. 580 1964.

Love, "Introduction" In: *Reducing breast cancer risk in women*, B. Stoll (Ed.), 1995.

Lubin et al., "Risk factors for breast cancer in women in Northern Alberta Canada as related to age at diagnosis," *Journal of the National Cancer Institute*, vol. 68, pp. 211–217 1992.

MacMahon et al., "Lactation and cancer of the breast: a summary of an international study," *Bulletin of the World Health Organization*, vol. 42, pp. 85 1970.

Marubini et al., "The relationship of dietary intake and serum levels of retinol and beta–carotene with breast cancer," *Cancer*, vol. 61, pp. 173–180 1988.

Matthews–Roth, *Curr. Top. Nutr. Dis. (New Prot. Roles Select Nutr.)* vol. 22, pp. 17–38 1989.

Matthews–Roth, *Pure Appl. Chem.* vol. 57, pp. 717–722 1985.

McTiernan et al., "Evidence of a protective effort of lactation on risk of breast cancer in young women," *American Journal of Epidemiology, 124*, 353–358, 1986.

Michnovicz et al., *How to reduce your risk of breast cancer.*, New York: Warner Books 1994.

Mori et al., *Jpn. J. Clin. Oncol.* 19: 373–379 1989.

Murrell, "Epidemiological and biochemical support for a theory on the cause and prevention of breast cancer," *Medical Hypotehses, 36*, 389–396, 1991.

Negri et al., "Intake of selected micronutrients and the risk of breast cancer," *International Journal of Cancer* vol. 65, pp. 140–144 1995.

Newcomb et al., "Lactatation and a reduced risk of premenopausal breast cancer," *New England Journal of Medicine*, vol. 330, pp. 81–87 1994.

Paganini–Hill et al., "Vitamin A, beta–carotene, and the risk of cancer: A prospective study," *Journal of the National Cancer Institute* vol. 79, pp. 443–448 1987.

Papanicolaou et al., "Exfoliative Cytology of the Human Mammary Gland and Its Value in the Diagnosis of Cancer and Other Diseases of the Breast," *Cancer*, vol. 11, No. 2, pp. 377–409, Mar.–Apr. 1958.

Parl et al., *Hum. Pathol.* 19: 960–966, 1988.

Patton et al. Carotenoids of human colostrums. Lipids. 1990, vol. 25, No.3, pp. 159–165.

Pertschuk et al., *Cancer*, vol. 66, 1663–1670 1990.

Peto et al., *Nature*, vol. 290, pp. 201–208 1981.

Petrakis et al., "Association of breast fluid coloration with age, ethnicity, and cigarette smoking," *Breast Cancer Research and Treatment*, vol. 11, pp. 255–262 1988.

Petrakis et al., "Association of race, age, menopausal status, and cerumen type with breast fluid secretion in non–lactating women as determined by nipple aspiration," *Journal of the National Cancer Institute*, vol. 54, pp. 829–833 1975.

Petrakis et al., "Cerumen phenotype and proliferative epithelium in breast fluids of U.S.–Born immigrant Asian women: A possible genetic–environmental interaction," *Breast Cancer Research and Treatment* vol. 16, pp. 279–285 1990.

Petrakis et al., "Cholesterol and Cholesterol Expoxides in Nipple Aspirates of Human Breast Fluid," *Cancer Research*, vol. 41, pp. 2563–2566, Jun. 1981.

Petrakis et al., "Correlation of breast fluid related to concentration of cholesterol, cholesterol epoxides, estrogen, and lipid peroxides," *American Journal of Clinical Pathology*, vol. 89, pp. 117–120 1988.

Petrakis et al., "Mutagenic Activity in Nipple Aspirates of Human Breast Fluid", *Cancer Research*, vol. 40, 188–189.

Petrakis et al., "Nipple aspirate fluids in adult non–lactating women–lactose content, cationic Na+, K+, Na+/K+ ratio, and coloration," *Breast Cancer Research and Treatment*, vol. 13, pp. 71–78 1989.

Petrakis, "Nipple Aspirate Fluid in Epidemiologic Studies of Breast Disease", *Epidermiologic Reviews*, vol. 15, No. 1, pp. 188–195 (1993).

Petrakis, "Physiologic, biochemical, and cytologic aspects of nipple aspirate fluid," *Breast Cancer Research and Treatments* vol. 8, pp. 7–9 1986.

Pitt "Vitamin A" In: *Fat soluble vitamins: Their biochemistry and applications*, A. Diplock (Ed.), pp. 1–75, London: Heinemann 1985.

Porter–Jordan et al., *Hematol. Oncol. Clin. North Amer.* 8: 73–100 1994.

Potishman et al., "Breast cancer and dietary and plasma concentrations of carotenoids and vitamin A," *American Journal of Clinical Nutrition*, vol. 52, pp. 909–915 1990.

Rohan et al., A population based case–control study of diet and breast cancer in Australia *American Journal of Epidemiology*, vol. 128, pp.478–489 1988.

Sarhadi et al., *Br J Plast Surg*, (8): 668–670, 1997.

Sartorius "Breast fluid cells help in early cancer detection," *Journal of the American Medical Association*, vol. 224, pp. 823–827 1973.

Sartorius et al., "Cytologic evaluation of breast fluid in the detection of breast disease," *Journal of the National Cancer Institute*, vol. 59, pp. 1073–1078 1977.

Sauter, et al.; "Nipple aspirate fluid: a promising non–invasive method to identify cellular markers of breast cancer risk"; British Journal of Cancer (1997) 76(4) pp. 494–501.

Seud et al., *J. Reprod Med.*, 38(6), 438–442, 1993.

Siskind et al., "Breast cancer and breastfeeding: Results form an Australian case–control study," *American Journal of Epidemiology*, vol. 130, pp. 229–236 1988.

Taylor–Papadimitriou et al., "Cell lineage and interactions in neoplastic expression in the human breast," In: *Understanding Breast Cancer*, M. Rich, J. Hager, & P. Furmanski (Eds.), pp. 215–246, New York: Marcek Dekker, Inc. 1983.

Van't Veer et al., "Dietary fiber, beta–carotene, and breast cancer: Results from a case–control study," *International Journal of Cancer*, vol. 45, pp. 825–828 1990.

Visozo et al., "Factors affecting protein composition of breast secretions from nonlactating women," *Breast Cancer Research*, vol. 23, pp. 251–258 1992.

Vizoso et al., Relationship Between Serum Prolactin Levels and Protein Composition of Breast Secretions in Nonlactating Women, *Journal of Clinical Endocrinology and Metabolism*, vol. 79, No. 2, pp. 525–529, 1994.

Wald et al., "Plasma retinol, beta–carotene, and vitamin E. levels in relation to further risk of breast cancer," *British Journal of Cancer*, vol. 49, pp. 321–324 1984.

Weisberger "Nutritional approach to cancer prevention with emphasis on vitamins, antioxidants, and carotenoids," *American Journal of Clinical Nutrition*, vol. 53, pp. 226–237 1991.

Wrensch et al., "Breast Cancer Incidence in Women with Abnormal Cytology in Nipple Aspirates of Breast Fluid," *American Journal of Epidemiology*, vol. 135, No. 2, 1992.

Wrensch et al., "Factors associated with obligating nipple aspirate fluid: Analysis of 1428 women and literature reviews," *Breast Cancer Research and Treatment*, vol. 15, pp. 39–51 1990.

Yoo et al., "Independent protective effect of lactation against breast cancer: A cast–control study in Japan," *American Journal of Epiderminology, 135*, 725–733, 1992.

Yuan et al., "Risk factors for breast cancer in Chinese women in Shanghai," *Cancer Research*, vol. 48, pp. 1949–1953 1988.

"Final Results of Ductal Lavage Study Presented At 23rd Annual San Antonio Breast Cancer Symposium: Pre-malignant and Malignant Cells Detected in Women at High-risk for Breast Cancer"; http://www.ductallavage.com/Product/Text/San_Antonio_release.html.

"Lancet Study Shows Promising New Breast Cancer Research Application Using Ductal Lavage"; http://www-.ductallavage.com/Product/Text/FINALPDHLancetreleased4.26.01htm.

"Study Demonstrates Ductal Lavage Collects Abnormal Breast Cells That Can Help Assess Breast Cancer Risk"; http://www.ductallavage.com/Product/Text/acog.htm; *University Physicians Medical Group*.

"Study: Ductal Lavage Shows Promise in Breast Cancer Detection"; IHS® Health Goup Medical Industry Today.htm.

* cited by examiner

DISPOSABLE PATIENT INTERFACE FOR INTRADUCTAL FLUID ASPIRATION SYSTEM

This is a continuation-in-part of U.S. patent application Ser. No. 09/870,402, filed May 30, 2001, which is incorporated in its entirety herein by reference.

The present invention relates to methods and devices for conducting noninvasive screening assays for indicia of breast cancer or other breast disease.

BACKGROUND OF THE INVENTION

Breast cancer is by far the most common form of cancer in women, and is the second leading cause of cancer death in humans. Despite many recent advances in diagnosing and treating breast cancer, the prevalence of this disease has been steadily rising at a rate of about 1% per year since 1940. Today, the likelihood that a woman living in North America will develop breast cancer during her lifetime is one in eight. The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection, there remain serious problems in distinguishing between malignant and benign breast disease, in staging known breast cancers, and in differentiating between different types of breast cancers (e.g. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (e.g. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have been identified to date, and many of these have been shown to have important value for determining prognostic and/or treatment-related variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., Cancer 66: 1663–1670, 1990; Parl and Posey, Hum. Pathol. 19: 960–966, 1988; Kinsel et al., Cancer Res. 49: 1052–1056, 1989; Anderson and Poulson Cancer 65: 1901–1908, 1989.

The utility of specific breast cancer markers for screening and diagnosis, staging and classification, monitoring and/or therapy purposes depends on the nature and activity of the marker in question. For general reviews of breast cancer markers, see Porter-Jordan et al., Hematol. Oncol. Clin. North Amer. 8: 73–100, 1994; and Greiner, Pharmaceutical Tech., May, 1993, pp. 28–44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which may be important oncogenes as well. Tumor growth can also be evaluated using a variety of growth factor and hormone markers (for example estrogen, epidermal growth factor (EGF), erbB-2, transforming growth factor (TGF).alpha.), which may be overexpressed, underexpressed or exhibit altered activity in cancer cells. By the same token, receptors of autocrine or exocrine growth factors and hormones (for example insulin growth factor (IGF) receptors, and EGF receptor) may also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes may occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

Thus, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which may predict responsiveness of a patient to specific drugs or treatment options.

Methods for detecting and measuring cancer markers have been revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modem immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining breast tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of breast cancer evaluation, the use of conventional or needle biopsy samples for cancer marker assays is often undesirable, because a primary goal of such assays is to detect the cancer before it progresses to a palpable or mammographically detectable tumor stage. Prior to this stage, biopsies are generally contraindicated, making early screening and low risk monitoring procedures employing such samples untenable. Therefore, there is general need in the art to obtain samples for breast cancer marker assays by less invasive means than biopsy.

Thus, serum withdrawal has been attempted for breast cancer marker assays. Efforts to utilize serum samples for breast cancer marker assays have met with limited success. The targeted markers are either not detectable in serum, or telltale changes in the levels or activity of the markers cannot be monitored in serum. In addition, the presence of breast cancer markers in serum may occur at the time of micro-metastasis, making serum assays less useful for detecting pre-metastatic disease. In contrast, fluid within the mammary glands themselves is expected to contain much higher and more biologically relevant levels of breast cancer markers than serum, particularly in view of the fact that 80%–90% of all breast cancers occur within the intraductal epithelium of these glands. Fluid within the breast ducts is expected to contain an assemblage and concentration of hormones, growth factors and other potential markers comparable to those secreted by, or acting upon, the surrounding cells of the alveolar-ductal system. Likewise, mammary fluid is expected to contain cells and solid cellular debris or products that can be used in cytological or immunological assays to evaluate intracellular or cell surface markers that may not be detectable in the liquid fraction of mammary fluid.

Previous attempts to develop non-invasive breast cancer marker assays utilizing mammary fluid samples have included studies of mammary fluid obtained from patients presenting with spontaneous nipple discharge. In one of these studies, conducted by Inaji et al., Cancer 60: 3008–3013, 1987, levels of the breast cancer marker carcinoembryonic antigen (CEA) were measured using conventional, enzyme linked immunoassay (ELISA) and sandwich-type, monoclonal immunoassay methods. These methods successfully and reproducibly demonstrated that CEA levels in spontaneously discharged mammary fluid provide a sensitive indicator of nonpalpable breast cancer. In a subsequent study, also by Inaji et al., Jpn. J. Clin. Oncol. 19: 373–379, 1989, these results were expanded using a more sensitive, dry chemistry, dot-immunobinding assay for CEA determination. This latter study reported that elevated CEA levels occurred in 43% of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al, inapplicable to the majority of women who are candidates for early breast cancer screening. In addition, the first Inaji report cited above determined that certain patients suffering spontaneous nipple discharge secrete less than 10 $\mu$l of mammary fluid, which is a critically low level for the ELISA and sandwich immunoassays employed in that study. It is likely that other antibodies used to assay other cancer markers may exhibit even lower sensitivity than the anti-CEA antibodies used by Inaji and coworkers, and may therefore not be adaptable or sensitive enough to be employed even in dry chemical immunoassays of small samples of spontaneously discharged mammary fluid.

In view of the above, an important need remains in the art for more widely applicable, non-invasive methods and devices for obtaining biological samples for use in evaluating, diagnosing and managing breast disease including cancer, particularly for screening early stage, nonpalpable breast tumors. Biological samples thus obtained can be used to evaluate, diagnose and manage breast disease, particularly by detecting or measuring selected breast cancer markers, or panels of breast cancer markers, to provide highly specific, cancer prognostic and/or treatment-related information, and to diagnose and manage pre-cancerous conditions, cancer susceptibility, breast infections and other breast diseases.

SUMMARY OF THE INVENTION

Disclosed is a disposable patient interface for use with an intraductal fluid aspiration device. More specifically, the interface comprises a flexible tubular membrane attached to a rigid cap at its proximal end. The cap contains a vacuum port for connection to a source of vacuum.

Preferably, the tubular membrane has an open end having an unstressed diameter within the range of about 2 inches to about 4 inches. Preferably, the opposite end of the tubular membrane has an unstressed diameter no more than about 4 inches. The tubular membrane is formed of a material exhibiting a high tear strength such that the membrane can be stretched up to 150%, or up to 200%, or more of its initial diameter without tearing. The tubular membrane has an unstressed axial length within the range of from about 1 inch to about 6 inches, and more preferably, within the range of from about 2 inches to about 4 inches.

In one embodiment, the tubular membrane is formed of a styrene block copolymer sold under the tradename KRATON™, and has a wall thickness no more than about 0.05 inches, and for some materials, no more than about 0.015 inches. The proximal cap may form an interior chamber and is preferably formed of a material exhibiting sufficient rigidity to resist collapse when experiencing a vacuum of at least about 150 mm Hg, and more preferably, resists collapse at 250 mm Hg or more.

The proximal cap may further be configured with a first retention structure to cooperate with a corresponding retention structure on a handpiece, thereby resulting in a releasable connection therewith. The retention structure may be in the form of a recess on either the cap or handpiece and a corresponding protrusion on the opposite piece for fitting with the recess. It may also be in the form of a rigid projection on the handpiece that impinges upon a smooth surface of the cap thereby interfering with its subsequent relative movement.

According to another aspect of the present invention, a method for making a disposable patient interface comprises the steps of molding the proximal cap and overmolding the flexible patient interface.

Further features and advantages of the present invention will become apparent to those of skill in the art in view of the detailed description of preferred embodiments which follows, when considered together with the attached drawings and claims.

DETAILED DESCRIPTION OF THE PREFERRED EMBODIMENT

Figure 1:
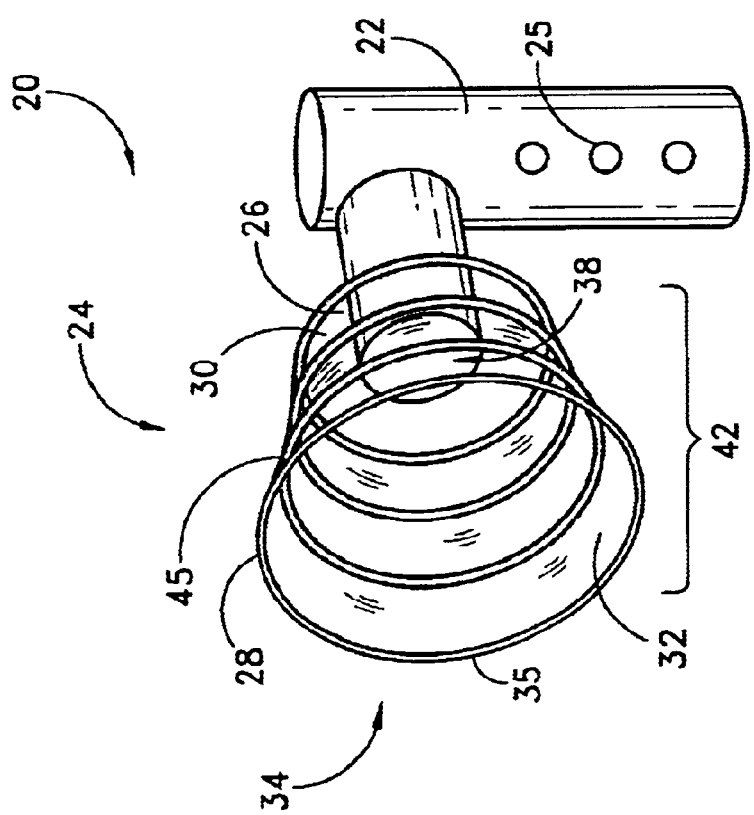
FIG. 1 is a schematic illustration of a portable, self-contained intraductal fluid aspiration device.

Referring to FIG. 1, there is illustrated a schematic representation of a portable, self-contained intraductal fluid aspiration device 20 in accordance with one aspect of the present invention. The aspiration device 20 includes a housing 22, for containing various controls and functional components of the device 20. One or more controls and/or indicators 25 may be provided on the housing, for controlling various aspects of the device such as suction, compression, and other features (e.g., heat, ultrasound) which may be included depending upon the intended functionality of the aspiration device 20. The housing 22 may be formed by extrusion, injection molding or other well known techniques from a suitable biocompatible material such as high density polyethylene, nylon, polyethylene terephthalate, or others well known in the art. The housing is preferably formed in an ergonomic configuration, to comfortably facilitate grasping in one hand during use.

The housing 22 is provided with a patient or breast interface 24, which may either be permanently attached to the housing 22 or removably attached such as for cleaning or disposal. Breast interface 24 has a proximal end 26, a distal end 28, and a body 30 extending therebetween. The interface 24 has a tissue contacting surface 32 defining a first concavity 34 for receiving a breast and a second concavity 38 for receiving a nipple. The tissue contacting surface 32 may be an integral surface on the body 30, or may comprise a separate interior liner which is adhered to or otherwise fit within and/or secured to the body 30.

The body 30 may be manufactured in any of a variety of ways, such as injection molding, blow molding tube stock within a tapered capture tube, or other known manners, using any of a variety of well known biocompatible polymeric materials. Preferably, the body 30 is transparent, which may be achieved by forming from polycarbonate, or other relatively clear materials known in the art. In one embodiment, the generally frusto-conical body 30 is sufficiently rigid to provide support for a flexible interior liner.

The dimensions of the interface 24 may be varied widely, as will be appreciated by those of skill in the art in view of the disclosure herein. In general, the distal end 28 of the flexible body 30 is provided with an elastic sealing ring 35 having an inside diameter within the range of from about 2" to about 10". The distal limit of the second concavity 38 has an inside diameter within the range of from about 1" to about 4". The first concavity 34 has an axial length from proximal end 26 to distal end 28 within the range of from about 0" to about 12", and, in many embodiments, within the range of from about 2" to about 6". The first concavity 34 has a generally conical or bell shaped interior configuration, as will be appreciated by those of skill in the art.

Preferably, the breast interface 24 is provided with a dynamic compression zone 42, having one or more compression elements 45 for compression in the mid breast region to facilitate intraductal fluid aspiration. Although the specific dimensions will vary from patient to patient, as well as with age and parity, the breast includes a plurality of ducts which are generally confluent in the direction of a plurality of external openings on the nipple. Most of the intraductal volume is contained in the distal one-half or one-third of the breast (from the patient's perspective). Thus, the inventors presently believe that a compression zone approximately centered around the midbreast region in an average patient and extending anatomically distally will optimize fluid transport in the duct.

Figure 2:
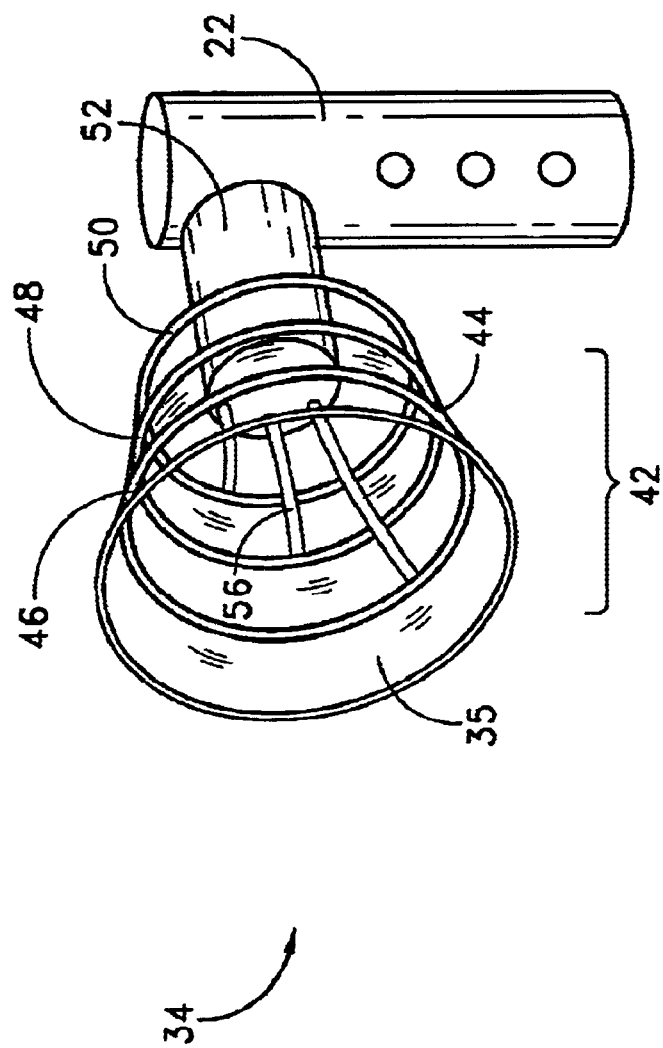
FIG. 2 is an illustration of a portable self-contained intraductal fluid aspiration device as in FIG. 1, schematically illustrating a plurality of annular compression rings.

Referring to FIG. 2, the dynamic compression zone 42 is schematically illustrated (not to scale) as comprising a plurality of annular compression rings 44, 46, 48 and 50. Preferably, the annular compression rings are in operative communication with a driver 52 in the housing 22, to permit sequential operation. One operation mode mimics a peristaltic motion such that tissue compression is accomplished sequentially proximally with respect to the device starting with compression ring 44 followed by compression ring 46 followed by compression ring 48 followed by compression ring 50. As will be apparent to those of skill in the art in view of the disclosure herein, any of a wide variety of compression ring numbers and configurations may be utilized in accordance with the present invention. Thus, the illustration of four compression rings in FIG. 2 is not considered limiting on the scope of the invention. In general, anywhere from about one to about twenty compression elements 45 may be utilized, in ring form or nonannular form, and, preferably, between about three and ten are contemplated in most embodiments.

The compression elements 45 may comprise any of a variety of structures, such as inflatable tubular elements or other inflatable structures, or mechanical compression elements such as rollers. In the illustrated embodiment, which is not drawn to scale in order to improve clarity, the dynamic compression zone 42 comprises a plurality of annular, inflatable, tubular compression rings each of which is connected to the driver 52 by a unique conduit 56. The driver 52 preferably includes a microprocessor or other central processing unit for sequentially driving the compression elements 45 as described previously. In one embodiment, the driver 52 includes a pump for controllably inflating and deflating each compression ring in response to the microprocessor and in accordance with the predetermined compression protocol. Inflation media such as air, water, or gel may be utilized, depending upon the desired performance characteristics. In one embodiment, a heat retaining gel such as morphing gel, available from Dow Corning, is utilized to enable the delivery of heat during the compression cycle.

The compression elements 45 may alternatively be connected to each other by a capillary tube or flow restriction orifice, or pressure relief valves to enable compression (inflation) in a predetermined sequence. Alternatively, the compression elements 45 may be in fluid communication with each other, with each having a wall with a unique durometer or elasticity such that each element inflates as a unique threshold inflation pressure is reached and/or exceeded.

The microprocessor may be programmed to a particular pumping and compression cycle characteristic, or may be adjustable by the user to optimize the aspiration function as desired. For example, compression cycles may be peristaltic, with a sequential compression pattern from chest wall (distal end 28) to the proximal end 26. Alternatively, the compression cycle may be non peristaltic pulsatile. Vacuum may be applied constantly throughout the pumping cycle, or may be pulsatile either in phase or out of phase with the compression cycles.

The aspiration device 20 is further provided with a vacuum generator such as a pump in the housing 22, in communication with the second concavity 38 by way of a vacuum conduit (not shown). Associated electronics, such as a power source and driving circuitry are preferably connected to a control 25 to enable the user to selectively activate and deactivate the vacuum. Alternatively, the pump and vacuum functions may be fully automatic, and preprogrammed into the micro-processor. The pump is generally capable of generating a vacuum within an operating range of from 0 (pump off) to about 300 mm/Hg. Although vacuum in excess of 300 mm/Hg may also be utilized, vacuum in this area or higher may cause rupture of microvasculature and is unnecessary to accomplish the objectives of the present invention. For this reason, limit valves may be provided in communication with the vacuum conduit, as are known in the art, to limit the vacuum to no more than about 200 mm Hg, or 250 mm Hg, or 300 mm Hg. Within the methods of the invention, negative pressures of 50–200 mm Hg are preferred, and these pressures are maintained, preferably intermittently, for approximately 1–15 minutes, depending on the sensitivity of individual patients, oxytocin dosage and other factors.

Figure 3:
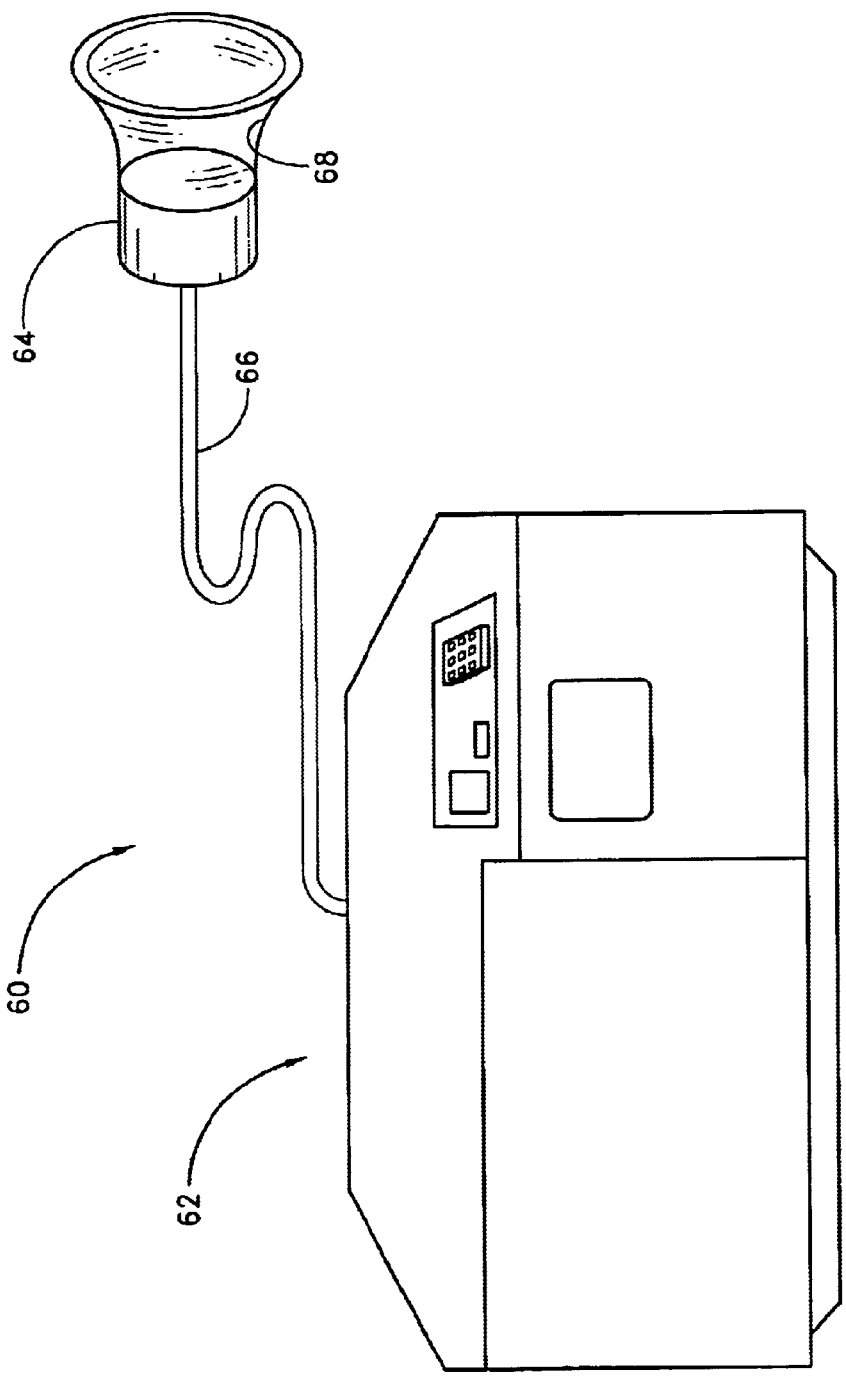
FIG. 3 is a schematic illustration of a desktop or cart top embodiment of an intraductal fluid aspiration device in accordance with the present invention.

The foregoing embodiment is useful in a variety of settings, particularly for in-home intraductal aspiration. In an alternative embodiment of the present invention, a desk top, or mobile cart top, unit 60 is provided, such as for the physician's office or other conventional clinical setting. See FIG. 3. The desk top intraductal fluid aspiration system 60 comprises a control unit 62, in communication with one or more power heads 64 by way of an elongate flexible control line 66. The power head 64 is provided with a disposable user interface 68 which may be similar or identical to the interface 24 described previously. In this embodiment, the interface 68 is preferably removably connected to the power head 64, to facilitate one time use and subsequent disposal of the interface 68. Alternatively, the entire interface and power head assembly may be one time use disposable.

The control 62 preferably includes the vacuum pump, and other driver circuitry and controls as may be needed depending upon the intended functionality of the desk top unit 60. For example, a vacuum pump (not illustrated) is in communication with the disposable user interface 68 by way of a vacuum lumen (not illustrated) extending throughout the length of the control line 66. Additional lumens or wiring extend through the control line 66 for accomplishing the peristaltic or other sequential compression motion of the dynamic compression zone 42 as has been discussed.

In either a diagnostic or non-diagnostic embodiment, a sample collector or reservoir may be positioned in fluid communication with the disposable user interface 68, to allow collection of intraductal fluid. The sample collector or container may be removable, such as to enable transport of collected intraductal fluid to a diagnostic laboratory or other facility for diagnostic analysis.

Preferably, the disposable user interface 68 is provided with a heat source, such as a heat retaining gel or other media for surrounding or contacting the interface 24, and/or for inflating the compression elements as has been previously discussed. Alternatively, resistance heating elements may be provided in the disposable user interface 68 or associated power head 64, powered by way of electrical conductors extending throughout the control line 66. In an embodiment where the dynamic compression zone 42 includes elements filled with a heat retaining gel or other media for retaining heat, the breast interface 24 may be removed and heated such as in a microwave oven or other heat source prior to use. An ultrasound source may also be provided in the control unit 62 or power head 64, for driving one or more ultrasound transducers in the power head 64 to assist in initial removal of keratin plugs that may occur at the opening of the ducts, and possibly also to serve as a heating source. Alternatively, a heating fluid may be circulated through a closed loop such as from a heater in the control unit 62, through a first lumen in control line 66 to a heat exchanger in the power head 64 or patient interface, and back through a second lumen in control line 66 to the control unit 62.

The volume of expressed mammary fluid will vary depending on a variety of factors, including patient sensitivity to oxytocin, if used, dosage of oxytocin delivered, time and pressure and other variables of breast pump administration, and other factors. For certain relatively low sensitivity breast marker assays, a volume of expressed mammary fluid of 300–500 μl is preferred to provide ample material for conducting the assay, and these volumes are expected to be obtainable from a substantial proportion of women treated according to the above methods. To express 300–500 μl of mammary fluid, some women will require repeated stimulation treatments, perhaps requiring pooling of mammary fluid samples obtained during multiple patient visits. However, for more sensitive assays of the invention, e.g. solid phase immunoassays, much smaller samples of 3 μl or less may be sufficient to carry out the assays. This is particularly so in the case of breast cancer markers that are naturally secreted into the mammary fluid and are therefore expected to be present in very high concentrations compared to, for example, breast epithelial cell surface antigens or intracellular antigens that may not be secreted.

Although one aspect of the present invention lies in the novel, non-invasive methods for obtaining biological samples from mammary fluid, an additional aspect of the invention involves the use of the collected sample for detecting and/or measuring important breast disease markers. The invention thus enables the convenient application of a broad range of assay methods incorporating known procedures and reagents for determining the presence and/or expression levels of breast disease markers, particularly breast cancer markers, in biological samples.

During or after the mammary fluid expression step, a biological sample is collected from the expressed mammary fluid. A range of suitable biological samples are contemplated and will be useful within the methods of the invention, including whole mammary fluid, selected liquid or solid fractions of the mammary fluid, whole cells or cellular constituents, proteins, glycoproteins, peptides, nucleotides (including DNA and RNA polynucleotides) and other like biochemical and molecular constituents of the mammary fluid.

Sample collection can be achieved simply by receiving the expressed mammary fluid within a suitable reservoir such as within or in communication with the concavity 38 with or without an absorptive sample collection media. Samples can be collected directly on to or subsequently exposed to conventional buffers, diluents, extraction or chromatographic media, filters, etc., to stabilize or prepare the sample for further processing or direct incorporation into a desired assay. In certain embodiments of the invention, the expressed mammary fluid is collected directly onto a solid phase medium, such as a microscopic glass slide, nitrocellulose filter, affinity column, dot blot matrix, cotton swab, or other like medium, that will selectively adsorb, bind, filter or otherwise process desired components of the mammary fluid, such as bulk or selected proteins, for convenient incorporation into a desired assay.

Alternatively, the sample may be collected from the patient's skin using any of the collection devices disclosed herein, following removal of the patient interface. The relatively high viscosity of the NAF sample tends to allow the sample to adhere to the patient's skin where it can be conveniently collected.

Figure 4:
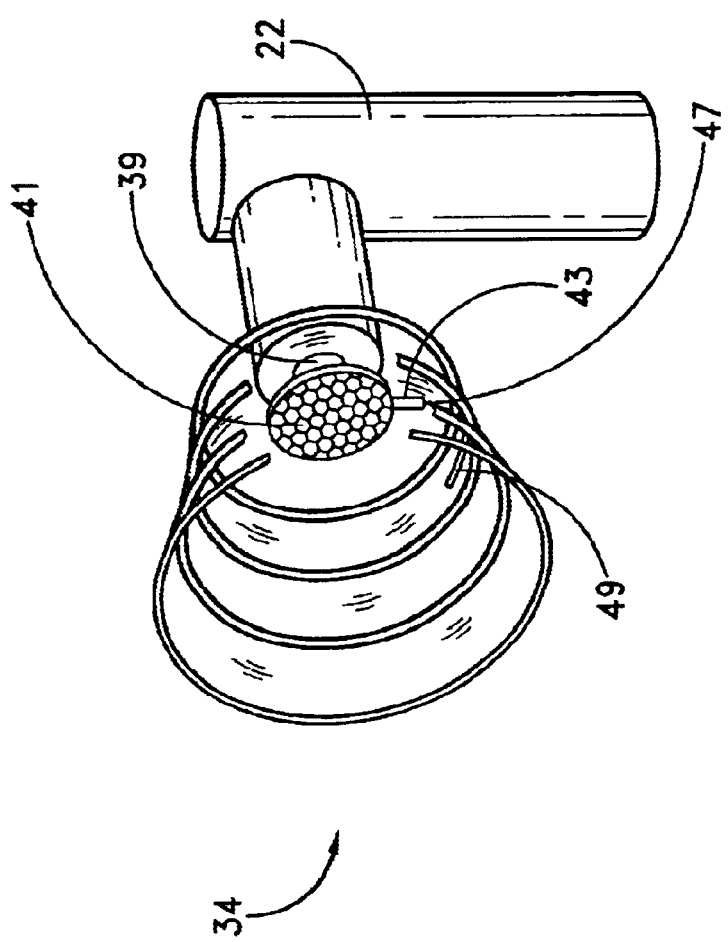
FIG. 4 is a schematic illustration of a sample collection patch, in communication with the flow path between the patient and a vacuum source.

Referring to FIG. 4, a flow path such as lumen 39 draws collected fluid from the patient through a sample collection patch 41. The sample collection patch 41 may be positioned directly against the external opening of the ducts, to minimize fluid loss in the device.

In the illustrated embodiment, the sample collection patch 41 is moveably positioned within the flow path, with a mild biasing force in the distal direction. In this manner, the patch 41 can maintain low pressure contact with the distal surface of the nipple throughout a range of axial positions along the longitudinal axis of the patient interface. Preferably, an axial range of motion is provided for at least the tissue contacting portion of the patch 41 of at least about 0.25 inches. In some embodiments, the range of from about 0.5 inches to about 2 inches or more may be accomplished. In the illustrated embodiment, the axial motion of the sample collection patch 41 is achieved by allowing bending or pivoting of the patch 41, throughout the patch and/or at a releasable attachment point 43 to either the patient interface 24 or the housing 22. Axial movement of the sample collection patch may alternatively be accomplished by mounting the sample collection patch on the surface of a compressible foam, which will compress in response to pressure from the patient. Alternatively, the compressible foam may form the sample collection media, without a separate patch, as is described below.

The sample collection patch 41 or other sample collection media may be removably attached to the aspiration device 20 such as by one or more releasable connections 47, which may comprise adhesive surfaces or mechanical interfit surfaces such as an annular recess for receiving the patch 41, radially inwardly extending tabs for receiving the patch 41, or others as will be apparent to those of skill in the art in view of the disclosure herein. The patch 41 may consist entirely of a flexible absorptive medium. Alternatively, the patch may include an absorptive medium in combination with a support structure such as a backing plate, or an annular ring for surrounding the patch 41, and facilitating releasable connection to the aspiration device 20.

The patch 41 is preferably removable from the aspiration device 20. The patch 41 may be removed through the first concavity or chamber 34, by hand or using tweezers, hemostats or other retrieval device. Alternatively, the patch 41 may be removed through a lateral opening 49 in the side wall of the aspiration device 20. As a further alternative, the patch 41 may be removed following disconnection of the patient interface 24 from the housing 22.

The patch 41 or distal surface of a solid sample collection medium such as a foam may have any of a variety of configurations, depending upon other aspects of the device design. In the illustrated embodiment, the patch 41 is a generally planar membrane. Alternatively, the patch 41 or patient contacting surface of a solid foam or other collection device may be conical or otherwise concave in the direction of the patient. The sample collection patch 41 or other sample collection structure may also have a component which extends distally towards the patient, from a lower portion of the patch 41, to capture any sample which may drop under the influence of gravity without first being absorbed by the patch 41.

The fluid capacity of the patch 41 or other collection media may be varied, depending upon the intended patient population and purpose of the aspiration. In general, sample sizes in the microliter or low milliliter range may be useful for different types of assays. For a certain patient populations, the volume of fluid expressed may reach in excess of 1 to 5 milliliters or greater, in which case a fluid collection chamber may be provided on the device in the area of the illustrated opening 49 on FIG. 4. Any of a variety of such variations will be apparent to those of skill in the art in view of the disclosure herein, taking into account the purpose of the aspiration.

The composition and construction of sample collection patch 41 will vary, depending upon the nature of the intended assay. For example, any of a wide variety of porous or absorptive materials may be utilized to collect cellular and cellular component samples which may be used for cytological exam. Materials such as conventional filter paper, cotton gauze, fiber webs such as knitted fabrics or nonwoven rayon or cellulose fibers may be used. A variety of microporous films comprising materials such as nylon 66, polycarbonate, modified polyvinyl fluoride and polyether sulfone may alternatively be used. Embodiments of the collection patch 41 which are intended to permit chemical or biochemical assays may additionally be provided with any of a variety of binders for either chemically binding with an analyte or adsorbing the analyte to be determined. The binder layer may additionally include a specific binding partner of the analyte to be determined, such as a polyclonal or monoclonal antibody or an antigen matched to a specific antibody desired to be measured in the extracted fluid. Other binding systems which are matched to the desired analyte or analytes may be readily adapted for use in the present invention, as will be understood by those of skill in the art. The range of contemplated sample collection procedures and materials that are useful within the invention is broad, and selected methods and materials will vary with each selected assay, as will be understood and readily practiced by those skilled in the art.

The sample collection patch may be constructed of any suitable material. In preferred embodiments, the sample collection patch includes a membrane or filtration medium upon, through, or in which a fluid sample is collected. The sample collection patch may be of any suitable shape. While circular or square patches are preferred for many applications, other shapes may also be used. The sample collection patch should be of sufficient size such that an adequate sample may be collected.

The sample collection patch may include a material capable of providing depth filtration or sieve filtration of a sample. In depth filtration, particulates are trapped both within the matrix and on the surface of the filtration medium. Depth filters are composed of random mats of metallic, polymeric, inorganic, or organic materials. Depth filters rely on the density and thickness of the mats to trap particulates and fluids, and generally retain large quantities of particulates or fluids within the matrices. Certain disadvantages of depth filters include media migration, which is the shifting of the filter medium under stress, and particulate unloading at high differential pressures. Advantages of depth filters include reduced cost, high throughputs, high volume-holding capacity, removal of a range of particle sizes, and high flow rates.

In sieve filtration, particulates larger than the pore size of a membrane are trapped, while smaller particulates pass through the membrane but may be captured within the membrane by some other mechanism. Sieve filtration membranes are generally polymeric films approximately 120 microns thick with a narrow pore size distribution. Certain disadvantages of sieve filtration include lower flow rates and lower particulate holding capacity. Advantages include absolute submicron pore size ratings, no channeling or bypass, capacity for retaining bacteria and particles, low extractables, sterilizable, and integrity testable.

In various embodiments, the sample collection patch includes one or more filtration media such as the filtration media manufactured by Pall Gelman Sciences of East Hills, N.Y. Such filtration media that may be suitable for use in particular assays of the various embodiments include filtration media originally developed for use in blood separations. Such filtration media may include polyester filtration media such as Pall Gelman's Hemasep™ modified polyester materials, polyether sulfone membranes such as the Presense™ membrane, Cytosep® single layer fiber composite membrane, and Leukosorb® medium. Other suitable filtration media may include the Predator™ membrane, a polyether sulfone membrane that is surface modified to possess nitro groups.

Pall Gelman's Biodyne® nylon 6,6 membranes may also be suitable for use in sample collection patches for certain assays. Unmodified Biodyne® nylon 6,6 membrane may be preferred for some applications. Alternatively, the Biodyne® nylon 6,6 membrane may be surface modified with quaternary ammonium groups so as to impart a positive charge to the pore surfaces, thereby promoting strong ionic bonding of negatively charged analytes. Likewise, the Biodyne® nylon 6,6 membrane may be surface modified with carboxyl groups so as to impart a negative charge to the pore surfaces, thereby promoting strong ionic bonding of positively charged analytes. Such carboxyl group surface-modified Biodyne® nylon 6,6 membranes may be derivatized via coupling reactions through the carboxyl groups at the pore surfaces.

In various embodiments other membranes may be preferred for use in sample collection patches, such as Biotrace® nitrocellulose membranes, Fluorotrans® polyvinylidene difluoride (PVDF) membranes, Immunodyne® ABC nylon 6,6 affinity membranes having a high density of covalent binding sites capable of permanently immobilizing proteins and peptides on contact, and Ultrabind™ aldehyde-modified polyether sulfone membranes capable of providing covalent binding to amine groups on proteins.

Various absorbent materials also available from Pall Gelman may also be used in certain embodiments, such as conjugate pads comprised of borosilicate glass with no binder or with polyvinylacetate (PVA) or another suitable binder, Loprosorb™ low protein binding hydrophilic fibrous medium, cellulose absorbent papers, Loprodyne® internally supported nylon 6,6 membrane with low protein binding, or Z-Bind™ post-treated modified polyether sulfone membrane.

Ion exchange membranes may be preferred for use in sample collection patches for certain assays. Such membranes may include Pall Gelman's Raipore™ ion-exchange polytetrafluoroethylene (PTFE) cationic or anionic membranes, and microporous ion exchange membranes constructed of polyether sulfone and possessing either sulfonic acid or quaternary ammonium groups on the membrane surface.

In various applications, it may be preferred to use a hydrophobic and/or oleophobic material in a sample collection patch. Materials suitable for use in such applications may include Pall Gelman's Hydrolon® nylon 6,6 membranes, Hydrolon® PTFE membranes, Supor® R polyethersulfone membrane, and Pallflex composite materials.

The above-mentioned filtration media available from Pall Gelman are representative examples of the wide variety of commercially available filtration media that may be suitable for use in sample collection patches. Various filtration media available from other manufacturers may also be suitable for use in sample collection patches, as may custom-manufactured filtration media. Suitable filtration media may include a single material, e.g., a single membrane, or may be a composite manufactured from two or more materials, e.g., various combinations of membranes, woven and nonwoven support materials, woven and nonwoven filtration media, barrier materials, and other materials. The sample collection patch may further include additional substances, such as reagents, buffers, probes, surfactants, binders, indicators, preservatives, and the like, such as may be useful in performing various assays.

Such filtration media may be bonded to a flexible structure, spring or other support to allow movement in and out of the collection chamber and to also allow ease of removal of the material for sample handling and removal. Alternatively, a closed-cell foam structure may be substituted for such media, thereby allowing movement in the chamber while maintaining contact with the nipple, either as a stand-alone collection medium or with a membrane bonded at the surface of the medium. Such media may also act as contamination barriers, protecting the powerhead circuit and pump system in the control console from contamination by body fluids in the negative pressure air path.

Thus, the present invention provides a method of screening intraductal breast fluid for one or more breast disease markers. The method comprises the steps of contacting the breast with a mechanical intraductal fluid aspiration device, and activating the device to apply compression and suction to the breast during a period of nonlactation to remove intraductal breast fluid. The fluid is thereafter screened such as by cytological examination and/or biochemical screening for breast disease markers. In one embodiment, the method further comprises the step of applying heat from the device to the breast.

There is also provided an intraductal breast fluid screening device. The device comprises a tissue contacting surface defining a first concavity for receiving a breast and a second concavity for receiving a nipple. A driver for imparting compressive force on at least a portion of the tissue contacting surface defining the first concavity is additionally provided. A vacuum conduit is provided in communication with the second concavity, and a sample collector may be provided in communication with the second concavity. The sample collector may be a reservoir, or an absorptive patch for absorbing or retaining a sample. Preferably, the collection patch is removable from the aspiration device.

The required sample size may vary, depending upon the intended assay or screening test. For example, relatively larger fluid volumes will be required for cytological examination as is well understood in the art. Relatively smaller sample sizes may suffice for monoclonal antibody or other specific binding chemistry assays or biochemical markers.

Figure 5:
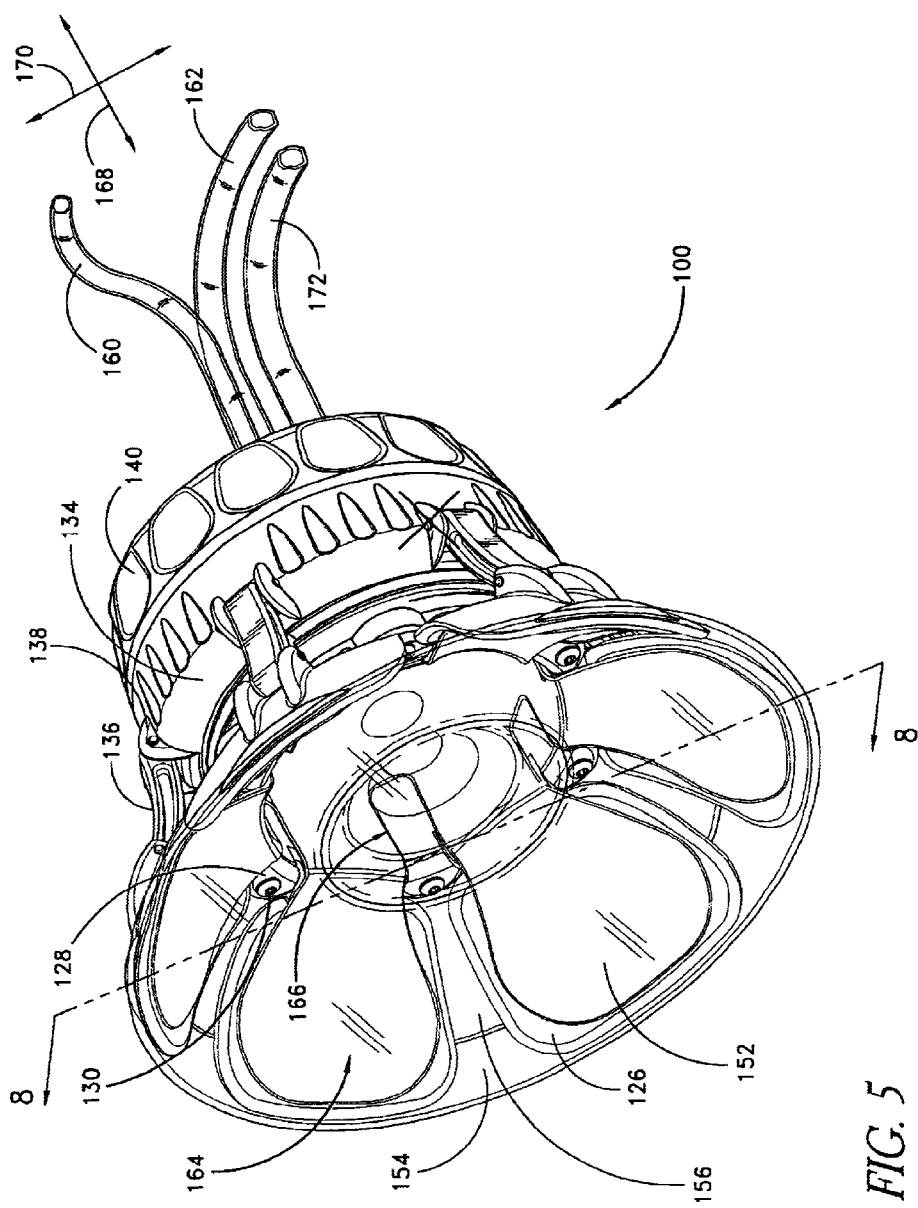
FIG. 5 is an isometric illustration of another embodiment of an intraductal fluid aspiration power head.

Referencing FIG. 5, an alternative embodiment of an intraductal fluid aspiration power head 100, or patient interface unit, in accordance with one aspect of the present invention is illustrated. The power head 100 is preferably formed in an ergonomic configuration to comfortably facilitate grasping in one hand during use and comprises a support such as a plurality of adjustable petals 126 that define an adjustable first concavity 164 for receiving a breast. There are generally between about two and about twenty petals, preferably, between four and eight petals, and six petals are present in one embodiment. The petals 126 are hingedly or otherwise movably connected to the main body (132 of FIG. 7) and are operatively coupled to a slide collar 134 via pinned links 136 or pivots.

A control is provided, to enable rough sizing of the device to accommodate a range of patient sizes. In the illustrated embodiment, the control comprises an adjustment ring 140. The slide collar 134 is carried by the adjustment ring 140, which is threaded onto the main body (132 of FIG. 7). As the adjustment ring 140 is rotated onto the main body 134, it translates linearly in a longitudinal direction 168. The slide collar 134 is in sliding engagement with the adjustment ring 140 such that the slide collar 134 does not rotate as the adjustment ring 140 is twisted about the main body 132.

In operation, the adjustment ring 140 is manually rotated about the main body, which causes the slide collar 134 to translate in a linear, longitudinal direction 168, thereby displacing the links 136, which cause the petals to pivot inward or outward about their connection point to the main body.

The support may take any of a variety of forms, and still accomplish the intended functional objective of providing support against which a movable element, such as an inflatable bladder (discussed below), will apply compressive pressure to the breast. Thus, the support may take the form of a rigid conical or hemispherical structure, or a flexible structure, such as a woven material or relatively inelastic polymeric wall. In general, however, the support is preferably adjustable in size to accommodate any of a wide variety of patients.

The illustrated support is one manner in which adjustability can be achieved. Alternatively, any of a variety of structures which allow the inside diameter of the distal opening of the support to be radially enlarged or reduced may be utilized. For example, the wall of the support may include a helical spring or other element which, when a distal end is rotated or otherwise manipulated relative to a proximal end, a radial reduction or enlargement is achieved. Alternatively, a flexible strap or band, such as a woven fabric, may be wrapped around and attached to itself using any of a variety of fasteners, such as hook and loop (e.g., Velcro®), snaps, or other fasteners known in the art. This construction is known in currently available blood pressure cuffs.

The foregoing structures take into account the usual circumstance that the range of inflation of the inflatable bladder as discussed below will generally be smaller than the range in patient sizes. Thus, the support can be rough adjusted so that the patient interface may be fitted to the patient with the inflatable bladders deflated, thereby ensuring that inflation of the inflatable bladders or other compression structure will accomplish a sufficient compression and minimize patient to patient performance variability. Additional details of the inflatable bladders will be discussed below.

Figure 11:
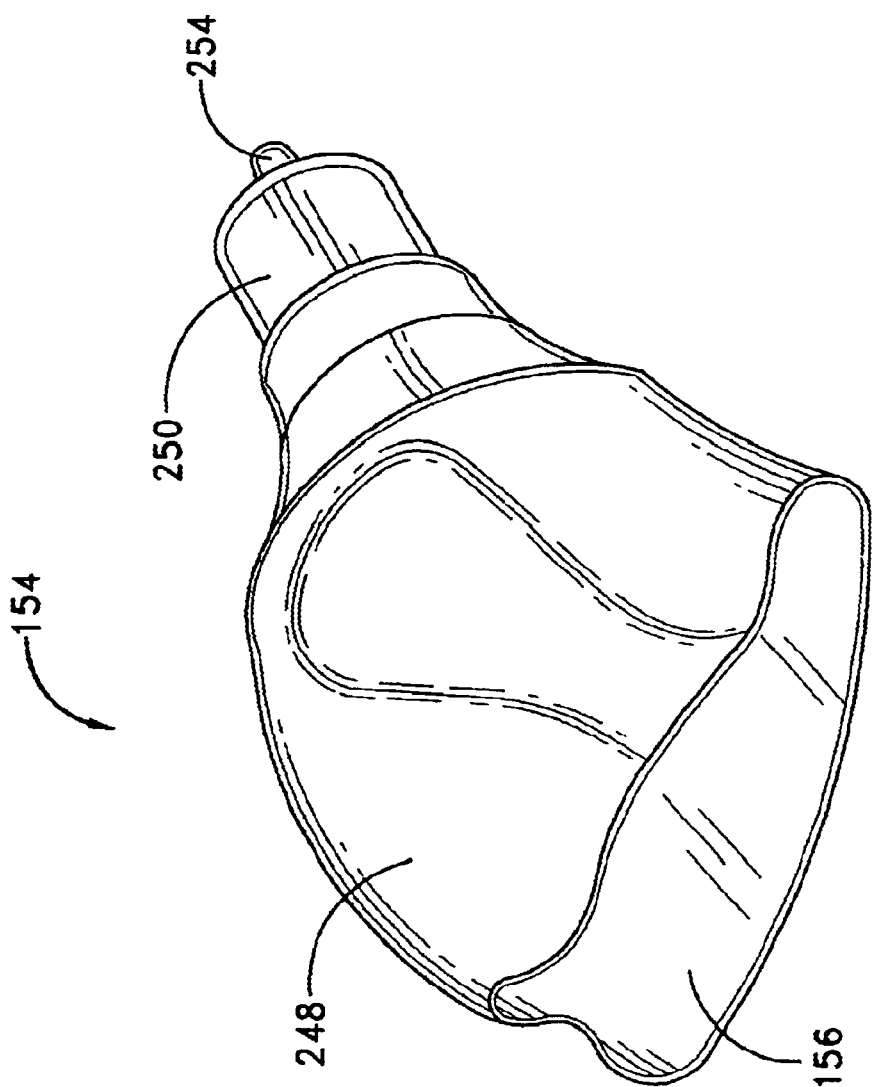
FIG. 11 is an illustration of one embodiment of a patient interface for use with an intraductal fluid aspiration power head.

The power head 100 is further provided with a patient interface 154, which may either be permanently attached to the power head 100 or removably attached such as for cleaning or disposal. In at least one embodiment, as shown in FIG. 11, patient interface 154 is a disposable sheath and includes a flexible frustoconical portion 248, or membrane, made of any of a variety of well known biocompatible polymeric materials such as silicone or any of a number of well known styrene block copolymers sold under the trade name Kraton, manufactured by Kraton Polymers. Examples of suitable materials may include, but are not limited to, styrene-butadiene-styrene (SBS), styrene-ethylene-butylene-styrene (SEBS), styrene-isoprene-styrene (SIS), or styrene-ethylene-propylene (SEP). Suitable polymers preferably exhibit a very low modulus of elasticity, allowing the material to stretch several times its original length, and a relatively high tear strength and optionally transparency, thus allowing an operator to see into the device to properly position a breast therein. The polymer is preferably bondable to polycarbonate or polypropylene, and is glutinous when contacted with certain materials thus allowing it to grip the petals 126 when mounted, while not adhering to latex, thereby allowing an operator wearing latex gloves to easily handle the patient interface 154.

The flexible portion 248 defines the tissue contacting surface 156 and is supported by the petals 126 which define the first concavity 164. The patient interface 154 is further configured with a relatively rigid proximal portion 250 configured to fit within the second concavity 166. The rigid portion 250 may be sized to receive a nipple, and has an inside diameter within the range of from about 0.5 inches to about 4 inches, and in one embodiment, has a length of about 1.5 inches and a diameter at its distal end of about 1.5 inches.

The rigid portion 250 terminates proximally at a tip 254 which has a lumen formed therein for allowing a vacuum conduit 160 to be in fluid communication with the interior of the patient interface 154. The proximal tip 254 may optionally contain a microbarrier for inhibiting contaminants from entering the patient interface 154 or being aspirated through the vacuum conduit 160. Moreover, the rigid portion 250 may carry a sample collection patch or other sample collector for collecting the aspirated fluid sample as has been discussed. The rigid portion 250 may be formed of a transparent, or semi-transparent, polymer such as, for example, polycarbonate or polypropylene to allow an operator to visually verify the position of the device on a patient. The removable patient interface 154 is removably connected to or otherwise fit within and/or secured to the power head 100.

Thus, in accordance with the disposable patient interface aspect of the present invention, there is provided a disposable patient interface for an intraductal fluid aspiration device. The interface comprises a sealing component and a vacuum chamber component. In the illustrated embodiment, the sealing component comprises a flexible tubular membrane, having a proximal end, a distal end and a passageway extending therethrough. The proximal end has a smaller cross-sectional area than the distal end, defining a generally frustoconical structure. A rigid proximal cap is provided on the proximal end of the flexible tubular membrane, and contains the vacuum chamber. A vacuum port is provided on the cap for connection to a source of vacuum.

The proximal cap 250 defines a chamber therein, and the cap exhibits sufficient structural integrity that it resists collapse when a vacuum of at least about 6 mm Hg is applied to the chamber. Preferably, the proximal cap 250 exhibits sufficient rigidity that it resists collapse when a vacuum of at least about 100 mm Hg is applied to the chamber.

The unstressed diameter of the distal end of the flexible tubular membrane 248 is generally within the range of from about 1 inches to about 6 inches, although other sizes may be utilized depending upon the desired clinical performance and intended patient population. Generally, the unstressed diameter of the distal end is no more than about 4 inches. The diameter of the distal end may be stretched to at least about 150% of its unstressed diameter without rupturing the membrane. Preferably, the diameter of the distal end may be stretched to at least about 200%, and, in some embodiments, as much as 400% or more of its unstressed diameter without rupturing the membrane.

In one application of the invention, the tubular member comprises a styrene block copolymer, having a wall thickness of no more than about 0.05 inches, and, in many embodiments, a wall thickness of no more than about 0.015 inches.

The axial length of the tubular membrane 248 from the distal end of the proximal cap to the distal end of the tubular membrane, along the surface of the membrane, is generally within the range of from about 1 inch to about 6 inches and, in many embodiments, within the range of from about 2 inches to about 4 inches.

In one embodiment, the proximal cap 250 comprises at least a first retention structure for releasable connection with a complementary second retention structure on the patient interface 154. The first retention structure may comprise a recess on the proximal cap or a projection on the proximal cap, and may be in the form of an annular bead or recess on the proximal tip 254.

In one embodiment, as shown in FIG. 5, the flexible portion 248 is stretched to fit over the distal periphery of the petals 126, and secured about a lip 190 formed on the outside surface of the petals. The patient interface 154 thus spans the gap between the individual petals 126 and thereby provides a flexible biobarrier to inhibit patient tissue from being pinched between the adjustable petals 126. The rigid portion 250 is removably mounted and snap fit or otherwise retained within the second concavity 166 as will be discussed in greater detail hereinafter.

Figure 6:
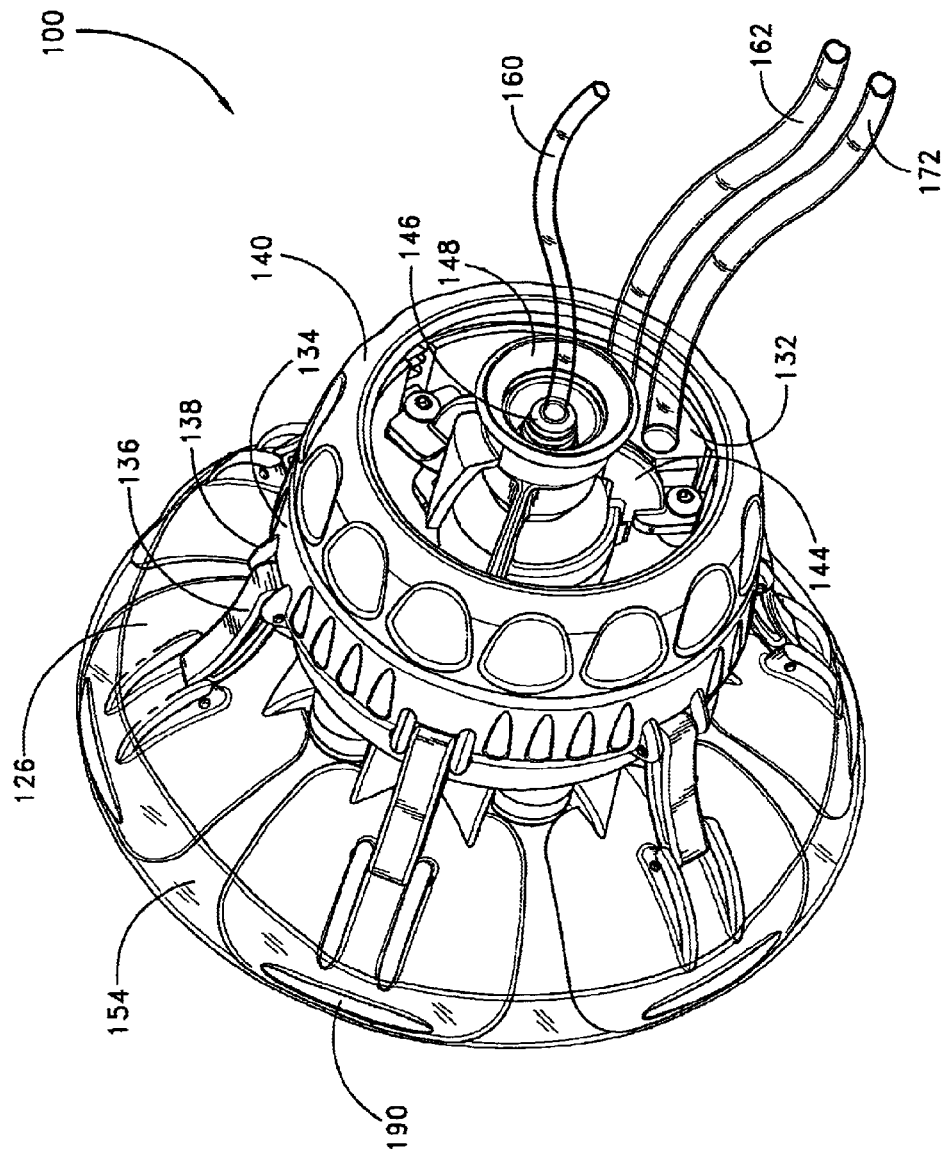
FIG. 6 is an illustration of an intraductal fluid aspiration power head as in FIG. 5, from a rear isometric view.

Referring generally to FIGS. 5 and 6, an inflatable bladder 152 conforms to the radially inwardly facing walls of at least the first concavity 164, and is sandwiched between the petals 126 and patient interface 154. The inflatable bladder 152 is preferably configured to receive an inflation media, thereby inflating and effectively reducing the volume within at least the first concavity 164, thereby applying a compressive force to a breast positioned therein. The specifics of the inflatable bladder will be discussed in greater detail hereinafter.

Referencing FIG. 6, the power head 100 is shown from a rear isometric view. From this perspective, the control tubes 160, 162, and 172 are illustrated. A vacuum conduit 160 is in communication with the interior chamber in the patient interface 154. In the illustrated embodiment, the vacuum conduit 160 passes through a tube grommet 146 and is supported thereby. The tube grommet 146 provides bending support to the vacuum conduit 160 and helps protect the tube from crimping or kinking. It further provides a fitting for receiving the distal tip 254 of the rigid mounting portion 250 of the patient interface 154, as will be shown and described hereinafter.

A pair of inflation conduits 162, 172, enter the power head 100 and are in fluid communication with the inflatable bladder 152 therein. The inflation conduits 162, 172 may be configured to cooperate in a variety of ways. For example, both conduits may deliver and subsequently withdraw inflation media to the bladder; each conduit may serve an isolated inflation chamber within the bladder; or one inflation conduit 162 may deliver inflation media, while the other conduit 172 may withdraw inflation media. The inflation media may be any gas, liquid, gel, or other media suitable for inflating the inflatable bladder 152. In an embodiment in which a heat source is provided remotely from the power head 100, the inflation media preferably also exhibits good heat transfer characteristics. Deionized water appears to have suitable performance. The inflation conduits 162, 172, are preferably formed of a material capable of withstanding hoop stress such that the inflation pressure inflates the inflatable bladder 152 rather than expands the inflation conduits 162, 172.

A release ring 148 is provided to release the patient interface from its mounted location and may optionally release the seal between the patient interface 154 and the patient upon completion of the intraductal fluid aspiration procedure, and will be discussed in greater detail in reference to FIGS. 10a and 10b. Alternatively, the vacuum release function may be assigned to the control unit.

Figure 7:
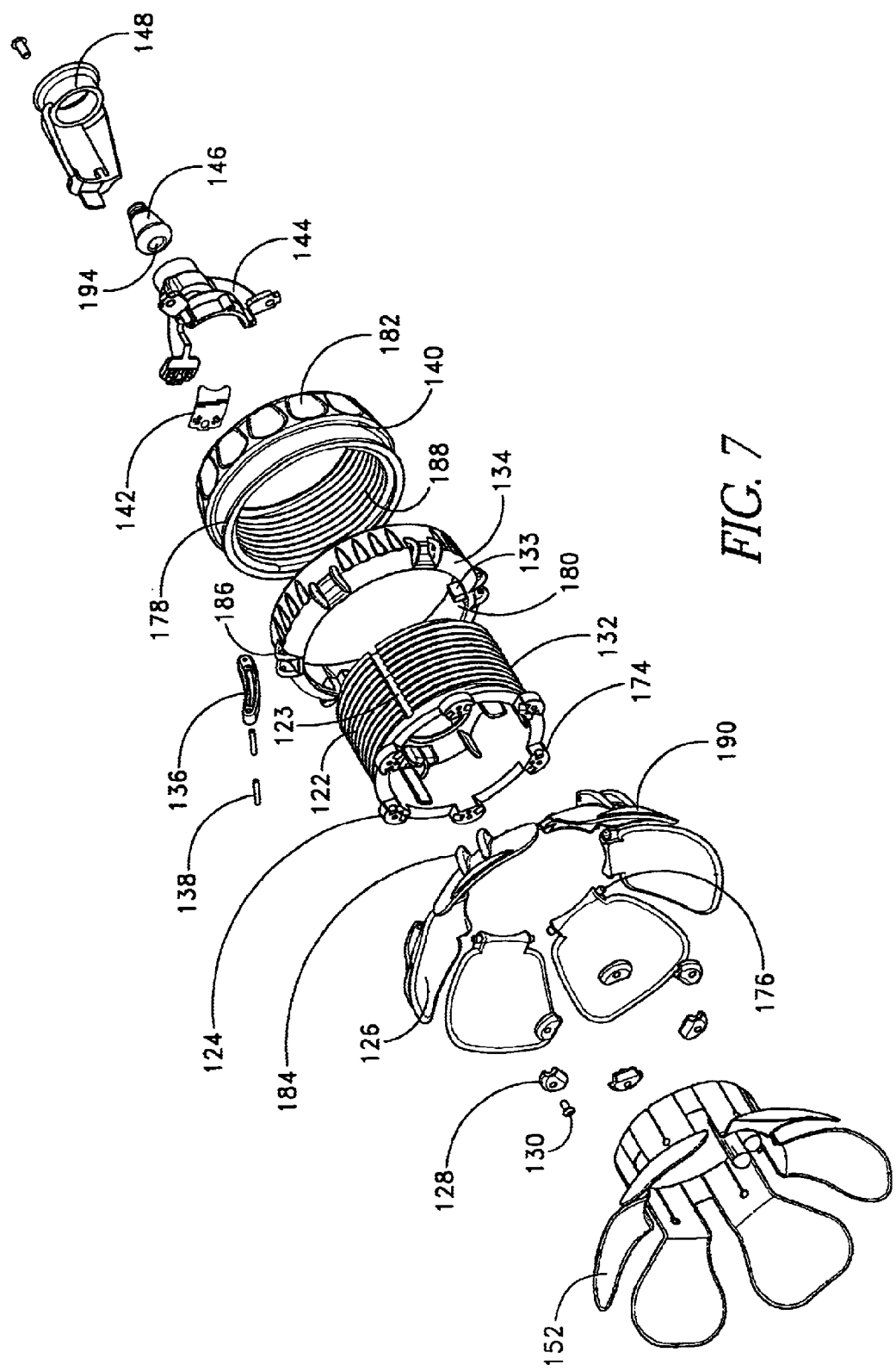
FIG. 7 is an exploded view illustration of the components of an intraductal fluid aspiration power head.

Turning to FIG. 7, an exploded view of the power head components is shown. For ease in describing the interrelation between the constituent components, they will be described in the context of assembly. Many of the following described features become more readily apparent in FIG. 8, and therefore, that figure is also referenced in relation to the following description.

The main body 132 has a plurality of petal mounting flanges 124 on its distal end, each having a threaded hole formed therein for receiving a threaded fastener 130, and at least one face groove 174 for receiving a portion of a petal 126. A plurality of petals 126 are provided each having an integral mounting pin 176 configured to fit within the face groove 174 formed into each petal mounting flange 124. A plurality of petal retainers 128 mount to the face of each petal mounting flange 124 to thereby secure the petal mounting pins 176 within the face grooves 174. In this manner, the petals 126 are hingedly mounted to the main body 132 and are pivotal about petal mounting pins 176. However, other methods of pivotal or bondable connection, such as through a compliant mechanism, may be used as should be apparent to those of ordinary skill in the art in light of the disclosure herein. This pivotal attachment allows for the power head 100 to be size-adjustable to fit different patients.

An adjustment ring 140 has a knurled portion 182 at a proximal end and an annular ridge 178 at a distal end. The knurled portion 182 provides a non-tangential surface for gripping to ease in threading the adjustment ring 140 on the main body 132. The annular ridge 178 cooperates with an annular groove 180, or equivalent structure, formed along the inside diameter of the slide collar 134 to engage the two components while inhibiting their disassembly. It is preferable that the adjustment ring 140 is free to easily rotate independent of the slide collar 134 during adjustment, and for this reason, materials exhibiting a relatively low coefficient of friction are used. Polymers and elastomers such as polybutylene terephthalate (PBT), acrylonitrile butadiene styrene (ABS), polyethylene, polypropylene, and polyurethane are preferred because of their high strength to weight ratios, low electrical conductivity, and ability to receive lubricant and colorant additives into their basic resins. Another benefit of using such materials is that they can be processed from raw materials into a final size, shape, and finish through any one of several basic casting operations, including injection molding, while maintaining the ability to be machined through any standard chip-producing, material-removal process to create details not available through standard casting processes. Additional components, such as the petals 126, main body 132, and links 136 are also preferably fabricated of similar materials to take advantage of these properties.

The main body 132 has outer body threads 122 formed thereon for cooperating with internal threads 188 of the adjustment ring 140. By rotating the adjustment ring 140 about the main body 132, the adjustment ring 140, and accompanying slide collar 134 are linearly translated. The main body 122 has one or more longitudinal grooves 123 that cooperate with corresponding tabs 133 inside the slide collar 134 to prevent the slide collar 134 from rotating about the main body 122. During assembly, the slide collar tabs 133 are inserted into the main body grooves 123 such that the tabs track within the grooves 123 and prevent subsequent rotation of the slide collar 134 relative to the main body 122. The slide collar 134 is coupled to mounting ribs 184 formed on the petals 126 via pinned links 136. The mounting ribs 184 are spaced to flank the link 136, and have a hole formed therethrough for receiving a pin 138. Likewise, the links 136 are hingedly attached to the slide collar 134 at mounting ribs 186. The pivotal mounting can be effected in any of a number of ways, and is not limited to a pin 138 as shown.

As the adjustment ring 140 is threaded about the main body 132, the attached slide collar 134 translates linearly, which imparts a linear motion to the links 136 which, in turn, causes the petals 126 to pivot about their attachment points. In this manner, the first concavity 164 is adjustable throughout a range between an initial open position, and an adjusted, patient form-fitting, position. In one embodiment, the petals are moveable between a fully open position, wherein the petals are substantially co-planar to each other and perpendicular to the longitudinal direction 168, and a fully closed position, wherein the petals 126 come together and contact along their edges, extending generally in parallel to the longitudinal axis. Thus, the minimum volume encompassed by the petals 126 is constrained only by the specific petal geometry. The petals 126 can be shaped such that the minimum volume of the first concavity 164 is substantially smaller than that achievable by the illustrated petal design.

Figure 8:
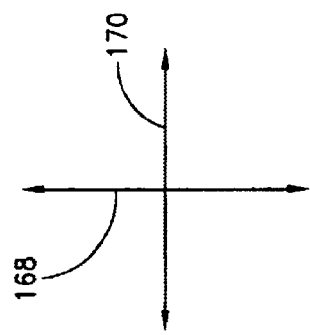
FIG. 8 is a cross-sectional view taken along the line 8—8 of FIG. 5.
Figure 8:
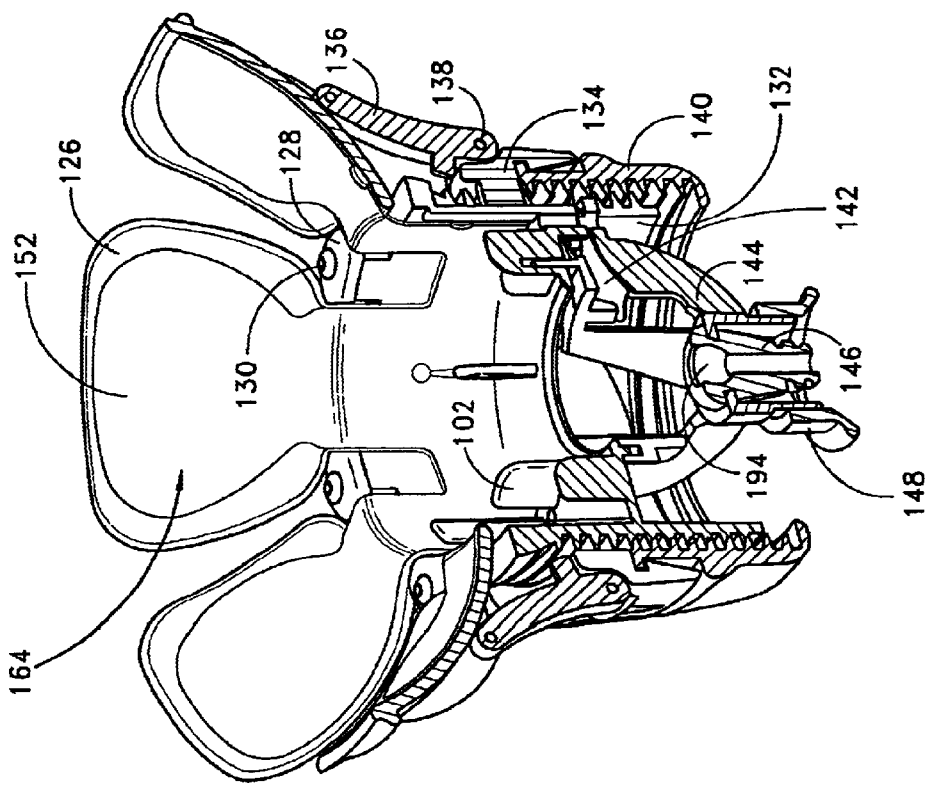

For example, FIG. 8 illustrates one embodiment of a petal design wherein each petal is identically sized and shaped. For example, each petal is about 2 in. wide in the transverse direction 170 by 1.75 in. high in the longitudinal direction 168, and is shaped such that it is concave inwardly in both a longitudinal 168 and transverse 170 direction. In this manner, the cooperating petals define a first concavity 164 that is substantially bowl or bell-shaped. The petals 126 could be sized and shaped differently to provide a more individual fit. For example, the petals 126 could be shaped and/or arranged to provide a substantially oval first concavity 164. Additionally, one or more petals 126 may be fixedly attached, with the remainder adjustable, or one or more petals 126 may exhibit different travel characteristics to result in various form-fitting shapes. Four, or three or two (e.g. clam shell configuration) petals may also be used, depending upon the desired manufacturing cost and clinical performance.

It is the adjustability of the first concavity 164, defined by the relative orientation of the plurality of petals 126 or other adjustable support structure, that allows the device to be adjustable to allow a single device to accommodate a range of patient sizes, to provide a comfortable fit and help create a seal between the power head 100 and the patient in order to effectively carry out the aspiration procedure.

Figure 13B:
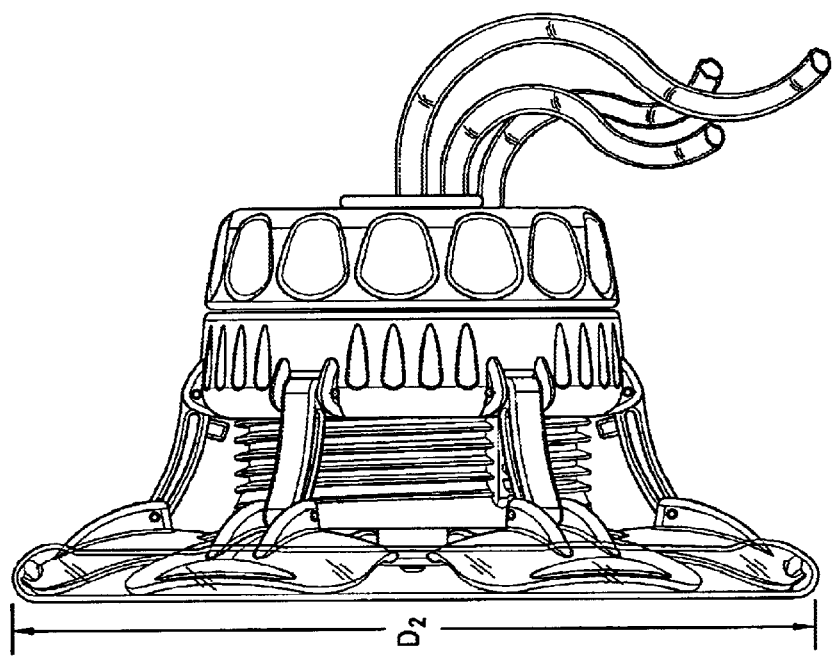
FIGS. 13A and 13B illustrate the petal range of motion demonstrating an initial starting position and a rough adjusted position.
Figure 13A:
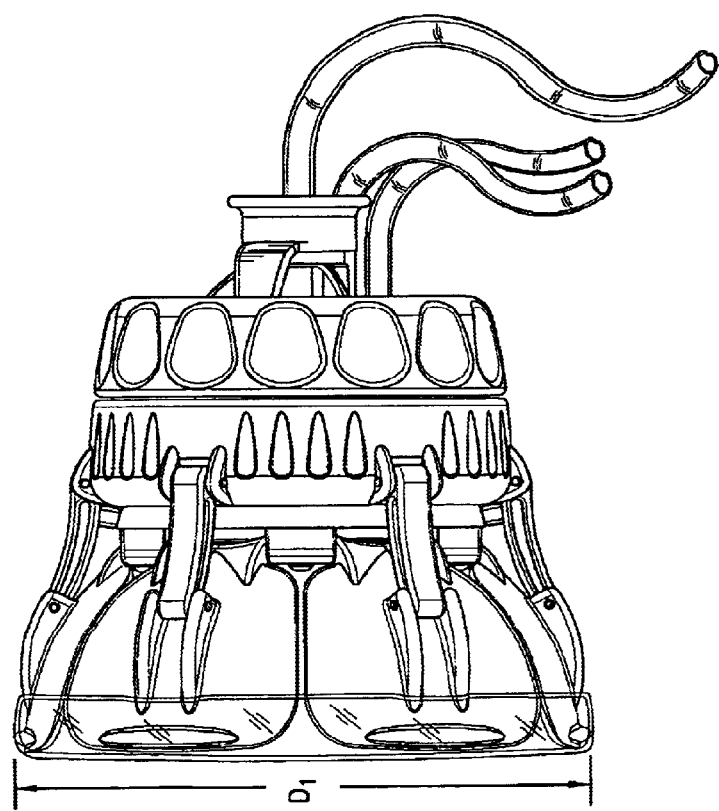

The dimensions and adjustability range of the first concavity 164 may be varied widely, as will be appreciated by those of skill in the art in view of the disclosure herein. In general, the distal opening defined by the distal limit of the petals 126 has an adjustable diameter within the range of from about 2 inches to about 12 inches. The adjustability is illustrated in reference to FIGS. 13A and 13B wherein the diameter "D" is adjustable within the range of from about 2 inches ($D_1$) to about 12 inches ($D_2$), and in certain embodiments, within the range of from about 3½ inches to about 6.5 inches. The second concavity 166 has an inside diameter within the range of from about 1 inches to about 4 inches. The first concavity 164 has an axial length within the range of from about 0 inches to about 12 inches, and, in many embodiments, within the range of from about 0 inches to about 6 inches. The first concavity 164 has a generally conical, hemispherical or bell shaped contoured interior configuration, as previously described, as will be appreciated by those of skill in the art.

Figures 14A, 14B:
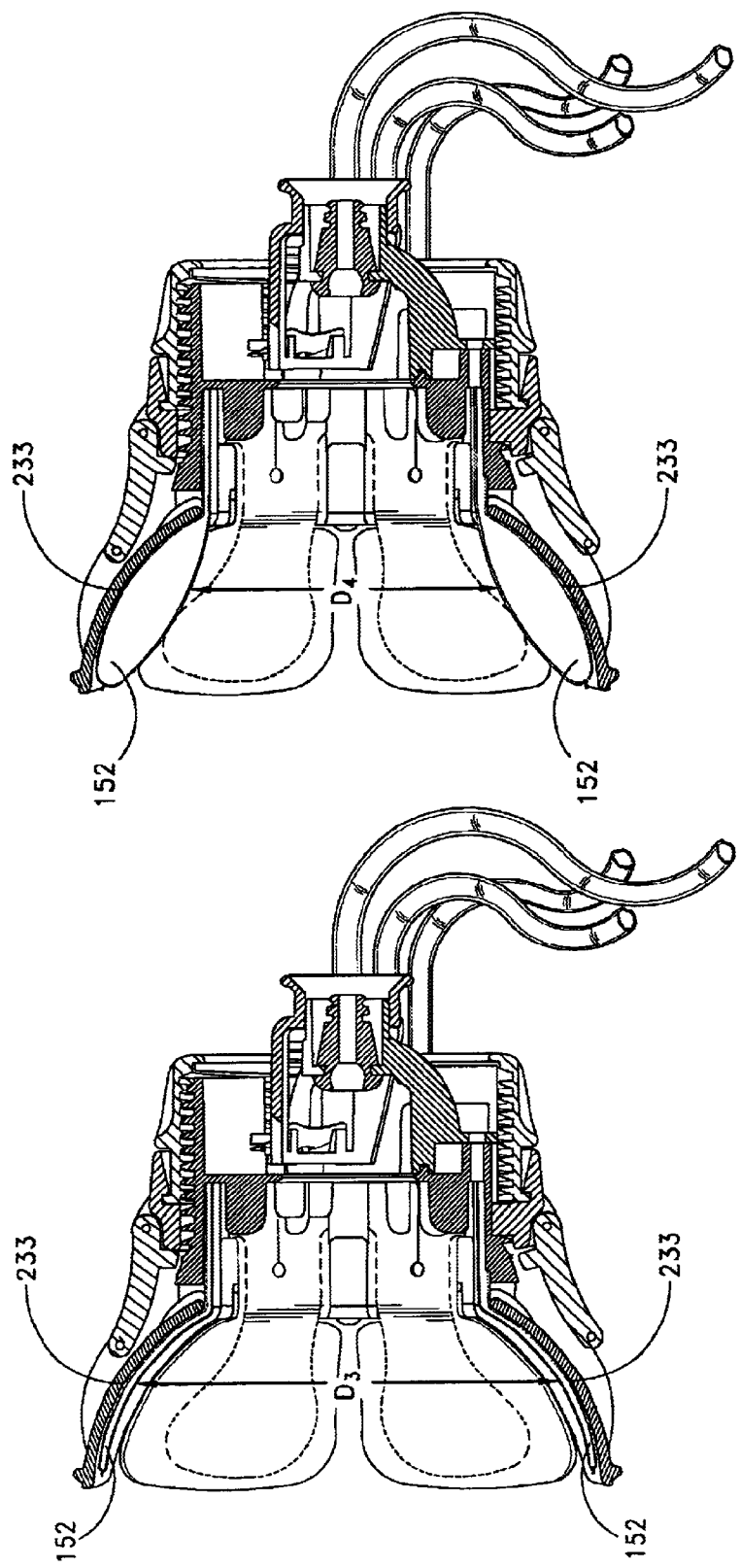
FIGS. 14A and 14B illustrate the varying diameter of the patient interface between a deflated and inflated state of the inflatable bladder of FIG. 9.

Referring briefly to FIGS. 14A and 14B, when the device is adjusted to fit a patient, for example, the inside diameter of the first cavity 164 is further movable between a first, large diameter $D_3$ when the bladder 152 is deflated and a second, reduced diameter $D_4$ when the bladder 152 is fully inflated. Diameters may be measured from a geometrical mid-point 233 on a first petal to a geometrical mid-point 233 on a second, opposing petal, as a reference. The difference between $D_3$ and $D_4$ provides an indication of the fully inflated thickness in the radial direction of the opposing lobes 152 of the bladder. In many embodiments of the present invention, the difference $D_3$–$D_4$ is within the range of from about 0.25 inches to about 2.5 inches. Generally, the difference $D_3$–$D_4$ is within the range of from about ½ inch to about 1½ inches. As will be appreciated by those of skill in the art, a $D_3$–$D_4$ difference of 1 inch means that the patient contacting surface of each opposing bladder lobe is movable throughout an operating range of about 0.5 inches.

Returning to FIG. 8, and with supplemental reference to FIG. 7, a tube support 144 is secured to the main body 132 by any suitable manner, such as threaded fasteners, and provides a support for the control tubes 160, 162, 172 extending therethrough. Tube support 144 additionally carries a tube grommet 146 which provides additional support to the vacuum conduit 160 as previously described. A release ring 148 is provided to disengage the patient interface rigid portion 250 from its mounted location. In one embodiment, the patient interface rigid portion 250 is secured through interaction with a leaf spring 142 configured to bite into the patient interface rigid portion 250 when the patient interface rigid portion is fully mounted. The release ring may optionally be used to release the vacuum seal between the patient interface 154 and patient. The purpose and operation of the release ring 148 and related components will be discussed in greater detail in connection with FIGS. 10a and 10b.

Figure 9:
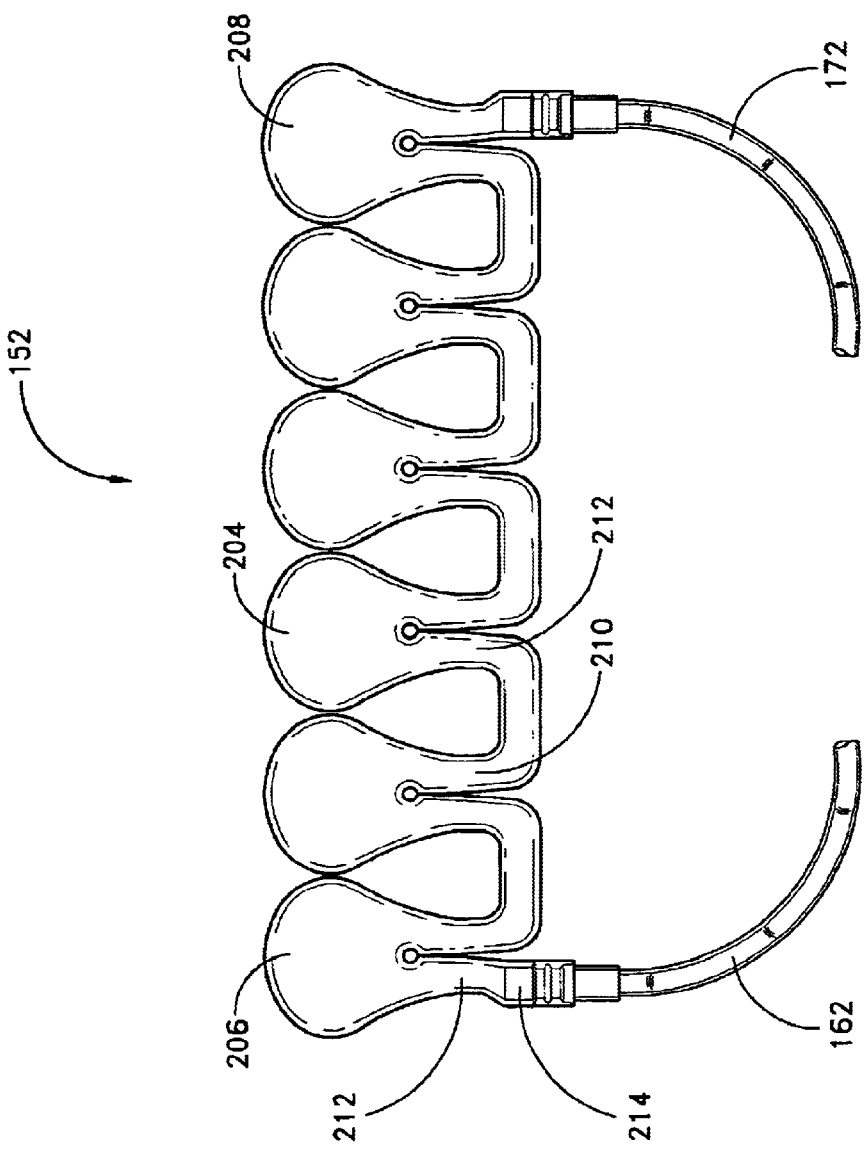
FIG. 9 is an illustration of one embodiment of an inflatable bladder for use with an intraductal fluid aspiration power head.

Referencing FIGS. 5 and 9, an inflatable bladder 152 is configured to fit at least within the first concavity 164. The main body 132 includes indexing structures such as one or more mounting tabs 102 (of FIG. 8) which position the inflatable bladder 152 toward the outer circumference of the main body 132. Furthermore, the inflation conduits 162, 172 pass through holes formed in the main body (132 of FIG. 6) and experience sliding friction therewith such that once the inflatable bladder 152 is positioned within the power head 100 and the inflation conduits 162, 172 are passed through the main body 132, the inflatable bladder 152 is inhibited from being dislodged from its desired position by the resistance of the inflation conduits 162, 172 from being slidably displaced. The inflatable bladder 152 is in fluid communication with inflation conduits 162, 172, and in one embodiment, one conduit is configured to deliver inflation media while the other conduit is configured to return inflation media.

In one aspect, the inflatable bladder 152 is configured to include a plurality of lobes 204, each corresponding to a petal 126, and may be optionally mounted thereto by adhesives, interference fit structures or other effective mounting methods. The lobes 204 are preferably generally rounded into a generally pear shape to allow the lobe to maintain a fairly uniform stress when under pressure. Each lobe 204 in the illustrated embodiment is sized to contain between about 1 mL and 100 mL of inflation media, and more particularly, to contain between about 5 mL and 20 mL. In one embodiment, the lobes 204 each have an inflated volume of about 10 ml, and have profile dimensions such that when fully inflated they extend radially inwardly through a thickness of about 1.0 inches.

In general, when the lobes 204 are fully inflated, they protrude inwardly between about 0.2 inches and about 2 inches from the inner wall of the petals 126, and in one embodiment, between about 0.75 inches and about 1.5 inches. Aside from the first and last lobe, 206 and 208 respectively, the outlet 210 of one lobe 204 connects to the inlet 212 of an adjacent lobe 204. Although in the illustrated embodiment, a plurality of lobes 204 are connected sequentially in series, parallel flow paths or other configurations are possible as described herein.

The inflation conduit 162 is securely attached to the inlet 212 of the first lobe 206 at 214 by any suitable manner, such as heat welding, by adhesives, crimping, and the like, and delivers inflation media to the first lobe 206 at a predetermined flow rate. In one embodiment, the inflatable bladder 152 is formed in a single die cut and heat welding step out of a material amenable to these techniques, such as, for example, polyurethane film having a thickness between about 0.003 inches and 0.030 inches. In one embodiment, a polyurethane film thickness of 0.015 inches is preferred. The inflation conduits 162, 172 may be permanently attached, such as by heat welding, during this single fabrication step. The inflation media is allowed to flow through the remaining lobes 204 and out through the final lobe 208, which terminates in a return conduit 172. The conduits 162, 172 may also be sealed to a reservoir, discussed below, to provide the closed loop. The closed loop may be charged with inflation media at the point of manufacture.

The return conduit 172 may have at least a portion that presents a smaller diameter for the media to flow through, thereby creating an amount of back pressure in the fluid system. Any of a variety of flow restrictors, such as apertures or reduced diameter flow paths may be used. In one embodiment, the return conduit 172 has a smaller inside diameter than the inflation conduit 162; however, the conduits 162, 172 could share a common diameter and a fitting along the return conduit 172 could include a portion having a diameter smaller than the inflation conduits 162, 172. In an alternative embodiment, a check valve may be placed along the return flow path 172 thereby allowing an adjustable restrictor for varying the back pressure which adjusts the inflation pressure. Additionally, an adjustable restrictor, such as a duck-bill flap, will allow the return path flow to be varied, including blocking the return flow path completely thereby causing a reverse inflation media flow to deflate the inflatable bladders 204 once the pump 262 is turned off. The flow restrictor may be located anywhere along the return path 172, including at the exit of the final bladder 208 or at the inlet of the fluid reservoir 260. Alternatively, the return conduit 172 could be constricted by external forces to reduce the flow therethrough and increase pressure in the upstream system. As a pump increases the flow of inflation media through the closed fluid system, the return line acts as a restrictor against which the pump creates pressure to inflate the lobes 204.

Thus, in accordance with the disposable fluid loop aspect of the present invention, there is provided a closed loop heating and/or compression system for a nipple fluid aspiration device. The closed loop system comprises a plurality of inflatable bladders or lobes for providing compression of a breast, a reservoir, and at least one fluid flow path for placing the bladders in fluid communication with the reservoir. As used herein, the bladder may be referred to either as a multiple lobed bladder, or a plurality of bladders in communication with each other, and/or a common inflation source, without any intended distinction.

In the illustrated embodiment, the fluid flow path comprises a movable wall, such as a compressible tube or reservoir. This allows forced circulation such as by exposing the tubing to a roller or platen pump, or by compressing the reservoir. The system generally comprises at least about three inflatable bladders, and, in one embodiment, about six inflatable bladders. Preferably, a heat exchange media, such as a fluid as has been described, is contained within the closed loop. Generally, each bladder has an inflated width of no more than about 3 inches and an inflated length of no more than about 4 inches. In many embodiments, each bladder has an inflated width of no more than about 2 inches and an inflated length of no more than about 3 inches.

The inflated thickness of each bladder may be varied widely, depending upon the desired performance characteristics. In general, each bladder has an inflated thickness of no more than about 1 inch, which provides a 2 inch dynamic range for the inside diameter of the concavity, during the compression and decompression cycles, as is discussed elsewhere herein.

A variety of modifications can be made to the disposable fluid loop, as will be apparent to those of skill in the art, in view of the structural support aspect of the present invention. In general, the inflatable bladder disclosed herein is one manner of providing a patient interface surface which is moveable between a first position in which the cavity has a relatively large cross sectional dimension and a second position in which the cavity has a relatively smaller cross sectional dimension. The difference between the relatively large and relatively small cross sectional dimensions of the cavity is the working range of the compression system.

In an alternate embodiment, the support may be movable throughout the working range, to provide compression. In this embodiment, the support may be moveable through a larger moving range to provide a rough adjustment as has been described elsewhere herein. Once the rough adjustment has been achieved, the support is then moveable throughout the smaller compression working range, using any of a variety of mechanical actuation devices such as a motor drive. In this embodiment, the inflatable bladder may be utilized to circulate a heating media, and not be utilized to impart compression. Alternatively, the support may be provided with an alternative heating mechanism such as an internal heating lumen for circulating a heated fluid, or internal electrical resistance coils or other heat source as will be appreciated by those of skill in the art. In such an embodiment, the inflatable bladder may be entirely eliminated.

An operator of the illustrated intraductal fluid aspiration system can directly control the inflation pressure of the inflatable bladder 152 by varying the pump speed. The inflation pressure is controlled by the pump speed, due to the flow restriction imposed along the return conduit. The pump preferably has safety features built in to limit its speed such that the inflation pressure provided by the pump cannot exceed the burst strength of the inflatable bladder 152, which in one embodiment, is about 1000 mm Hg. Alternatively, limit valves may be provided in communication with the inflation conduits 162, 172, as is known in the art. The operating pressure within the inflatable bladders during the compression cycle preferably does not exceed about 1000 mm Hg, and more preferably does not exceed about 420 mm Hg.

Referring back to FIG. 5, the inflatable bladder 152 creates a compression zone to facilitate intraductal fluid aspiration. As described, the inflatable bladder 152 is preferably in operative communication with an external inflation driver (not shown) through one or more inflation conduits 162, 172. In one embodiment, the inflatable bladder 152 has a single inflation chamber and is operable between a deflated state and a fully inflated state in which the interior pressure of the inflation media reaches a constant pressure. In another embodiment, a plurality of discrete inflation chambers are provided within the inflatable bladder 152 and are selectively inflated to create various compression modes. In one embodiment, the compression mode mimics a peristaltic motion such that tissue compression is accomplished sequentially proximally. This may be accomplished by selectively inflating a plurality of inflation chambers in fluid communication with each other, with each having a wall with a unique durometer or elasticity such that each inflation chamber inflates as a unique threshold inflation pressure is reached and/or exceeded. Alternatively, a plurality of inflation chambers may be interconnected in series by valves that open at sequentially greater pressures thereby sequentially inflating the chambers as the inflation pressure increases.

By inflating the inflatable bladder 152, the volume within the first and second concavities 164, 166 is effectively reduced, thereby applying a circumferential compressive force to a breast positioned therein. The inflatable bladder 152 is configured such that the compressive force is applied at a location that is anatomically adjacent or proximal to a patient's lactiferous sinus. Thus, the geometric center of each lobe is generally positioned no more than about three inches from the distal tip of the nipple. In this way, the intraductal fluid is encouraged to flow anatomically distally and is therefore expressed.

As discussed above, the inflation pump may be programmed to a particular compression cycle characteristic, or may be adjustable by the clinician to optimize the aspiration function as desired. For example, compression cycles may be peristaltic, with a sequential compression pattern from the patient's chest wall to an anatomically distal end. Alternatively, the compression cycle may be non peristaltic cycles, and may be pulsatile within each cycle. In one embodiment, a roller pump provides pulsatile inflation of the inflatable bladder 152 at a pulse rate between about 50 and 600 cycles per minute, which may add to the patient's comfort during the procedure.

The inflation cycle may be sinusoidal having a period of between about 1 and 20 cycles per minute. In one application of the invention, each compression cycle lasts about 10 seconds from empty to empty. A ten second pulse with a sinusoidal wave form thus produces approximately 6 inflation cycles per minute. Inflation cycles per minute may range from about one to about 20 or 30 cpm. In another embodiment, there may be a single inflation cycle during the aspiration procedure in which the inflatable bladder 152 is inflated under pulsatile pressure throughout the procedure. It should be readily apparent to those of ordinary skill in the art that various inflation cycle modes could be substituted for those described herein without departing from the scope of the claims.

In one embodiment, the inflation conduits 162, 172 are part of a closed fluid loop which includes a fluid reservoir (260 of FIG. 12), a first inflation conduit 162, the inflatable bladder 152, and a second inflation conduit 172. In referring to a closed fluid loop, it is to be understood that the term "fluid" means any gas, liquid, or gel suitable for use as inflation media. The same is true when referring to inflation fluid. The closed fluid system is thereby easily removed from the system and replaced and may be disposed of as desired. Furthermore, a closed fluid system provides convenience in setup and operation of the intraductal fluid aspiration system in addition to patient and device safety by keeping the fluid confined.

Inflation media such as gas, liquid, or gel may be utilized depending upon the desired performance characteristics. In one embodiment, a heat retaining gel such as morphing gel, available from Dow Coming, is utilized to enable the delivery of heat during the compression cycle. In another embodiment, deionized water is used as the inflation media, which offers a low electrical conductivity and resists algae and bacteria growth.

In cooperation with the applied compression, a vacuum is created by first forming a seal between the patient interface 154 and the patient. Generally, the rigid portion 250 creates a concavity for receiving a nipple and contacts the patient at a circumscribing location thereto. An external vacuum generator, such as a pump (230 of FIG. 12), applies a negative pressure in the second concavity 166 through a vacuum conduit 160, which removes any trapped air within the concavities 164, 166, thereby creating a vacuum therein and securely sealing at least the rigid portion 250 to the patient. Vacuum may be applied constantly throughout the pumping cycle, or may be pulsatile either in phase or out of phase with the compression cycles.

The pump 230 is generally capable of generating a vacuum within an operating range of from 0 (pump off) to about 260 mm Hg. Although vacuum in excess of 260 mm Hg may also be utilized, vacuum in this area or higher may cause rupture of microvasculature and is unnecessary to accomplish the objectives of the present invention. For this reason, limit valves may be provided in communication with the vacuum conduit, as are known in the art, to limit the vacuum to no more than about 150 mm Hg, or 200 mm Hg, or 250 mm Hg. Within the methods of the invention, negative pressures of 150–250 mm Hg are preferred, and these pressures are maintained, for approximately 1–15 minutes, depending on the sensitivity of individual patients, oxytocin dosage and other factors. The pressure may be maintained constantly throughout the aspiration procedure, or may be pulsatile.

Preferably, the power head 100 is provided with a heat source, such as a heated inflation media for inflating the inflatable bladder 152. Alternatively, resistance heating elements may be provided in the petals 126 and/or patient interface 154, powered by way of electrical conductors extending throughout the power head 100. In an embodiment where the patient interface 154 is filled with a heat retaining gel or other media for retaining heat, the patient interface 154 may be removed and heated such as in a microwave oven or other heat source prior to use. An ultrasound source may also be provided remotely or in the power head 100, for driving one or more ultrasound transducers in the power head 100 to assist in initial removal of keratin plugs that may occur at the opening of the ducts, and possibly also to serve as a heating source.

Alternatively, the inflation media may be circulated through a heater 264, through a first inflation conduit 162 into the inflatable bladder 152, and back through a second inflation conduit 172 to maintain an elevated inflation fluid temperature within the inflatable bladder 152. By circulating heated fluid through the closed loop the temperature (and inflation pressure) within the inflatable bladder 152 may be conveniently controlled. Preferably, temperatures in the range of about 30° C. to about 55° C., and more preferably within the range of from about 37° C. to about 50° C., and in one embodiment, 45° C. are maintained at the patient contact surface. There is a measurable heat loss as the heated inflation media travels through the inflation conduits 162, 172, and into the inflatable bladder 152, therefore, the media is preferably heated to a temperature slightly higher than desired. For example, a 46° C. temperature at the reservoir in one embodiment of the invention produces a patient contact surface temperature of approximately 39.5°–40.5° C. It is believed that the applied heat may lower the viscosity of the intraductal fluid in addition to overcoming physiological patient resistance to aid in fluid aspiration.

Figure 10B:
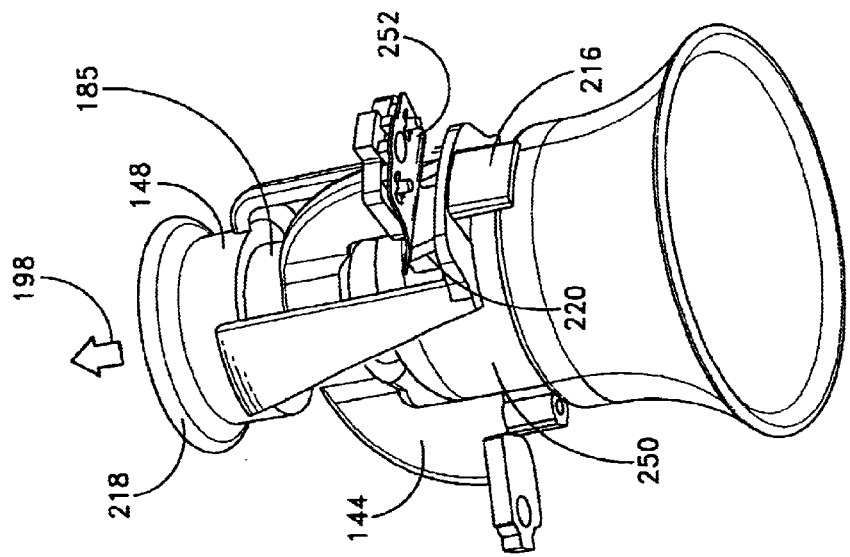
FIG. 10b is an illustration of a release mechanism in a disengaged position.
Figure 10A:
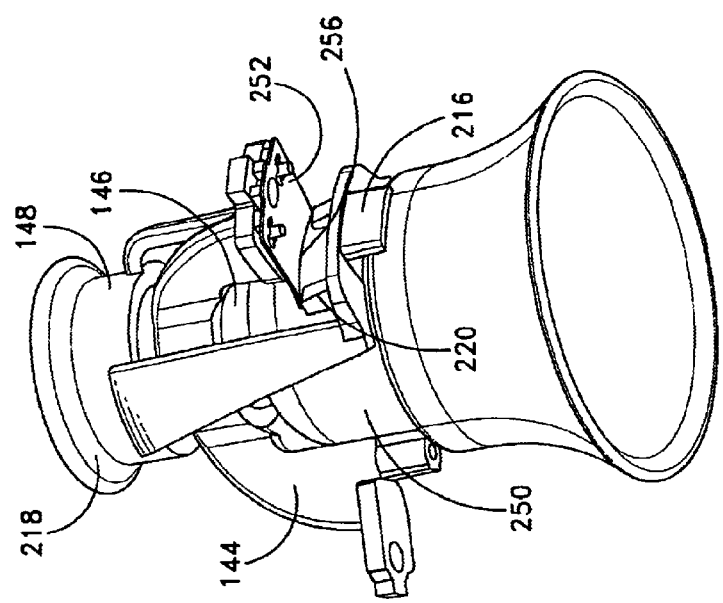
FIG. 10a is an illustration of a release mechanism for use in conjunction with an intraductal fluid aspiration power head.

Referring to FIGS. 10A and 10B, a release ring 148 is provided to disengage the patient interface rigid portion 250 from its mounted location. Additionally, the release ring 148 may optionally be used to release the vacuum created within the second concavity 166 and thereby break the seal between the patient and patient interface 154. The release ring 148 has a handle 218 having a bore therethrough for slideably mounting to a boss 185 of the tube support 144. The release ring 148 is preferably formed of cast polymer as previously described herein. The release ring 148 has a shelf portion 220 for interacting with a leaf spring 252 that is cantilevered to the tube support 144. The leaf spring 252 contacts the shelf portion 220 and biases the release ring 148 in a distal direction. The release ring 148 further includes an alignment flange 216 that fits into an alignment slot (not shown) formed in the main body 132 to ensure to proper mating of the constituent components.

The tube support 144 and release ring 148 define an open space for receiving the rigid portion 250 of the patient interface 154. As the patient interface 154 is mounted to the power head, the rigid portion 250 is pushed into the cavity defined by the tube support 144 and release ring 148 until the distal tip 254 enters the vacuum cavity 194 (of FIG. 8) formed in the tube grommet 146, and the rigid portion 250 is seated against the tube grommet 146 such that the malleable tube grommet 146 compresses against the rigid portion 250 and forms an airtight seal therewith.

The leaf spring 252 has a concave edge 256 for mating with the substantially cylindrical rigid portion 250 of the patient interface 154. As the distal tip 254 is forced into the vacuum cavity 194, the concave edge 256 of the leaf spring 252 contacts a portion along the outer periphery of the rigid portion 250. As the rigid portion 250 slides past the leaf spring 252, the leaf spring 252 resiliently bends in the direction of travel of the rigid portion 250, thus allowing the rigid portion 250 to slide by without impeding the movement thereof. Once the rigid portion 250 is mounted, the leaf spring 252 impedes the rigid portion 250 from dislodging from its mounted location. The concave edge 256 of the leaf spring 252 impinges upon the periphery of the rigid portion 250 thereby constructively interfering with the undesired withdrawal of the rigid portion 250 from its mounted location. In this way, the rigid portion 250 of the patient interface 154 is securely mounted thereby creating a substantially airtight seal with the vacuum cavity 194 of the tube grommet 146.

Upon completion of the procedure, the vacuum pressure is released to remove the power head 100 from the patient. This may be accomplished by actuating the release ring 148. As the handle portion 218 of the release ring 148 is manually actuated in a device proximal direction 198, the release ring shelf 220 elastically deforms the leaf spring 252 such that the patient interface rigid portion 250 is no longer constrained in its mounted location. The patient interface flexible portion 248, by virtue of being stretched to mount over the petals 126, is in tension, such that a releasing force is translated to the patient interface rigid portion 250. As the leaf spring 252 is deformed such that it no longer contacts the outer periphery of the patient interface rigid portion 250, the tension from the patient interface flexible portion 248 causes the distal tip 254 of the rigid portion 250 to withdraw from the vacuum cavity 194 thereby breaking the vacuum seal and allowing the power head 100 to be removed from a patient.

Alternatively, the vacuum pressure may be released by a control unit microprocessor protocol. For example, the external vacuum pump (not shown) may be configured with a release valve that is selectively operable to interrupt the vacuum. As another alternative, the vacuum pump may be reversible, thereby creating a positive pressure within the second concavity 166 further easing the disconnection with the patient. In another embodiment, a valve may be present along the vacuum conduit 160, or within the first or second concavities 164, 166, for releasing the vacuum. It will be apparent to one of skill in the art that there are a variety of ways to break the vacuum seal that are not disclosed herein yet are contemplated as being within the scope hereof.

Figure 12:
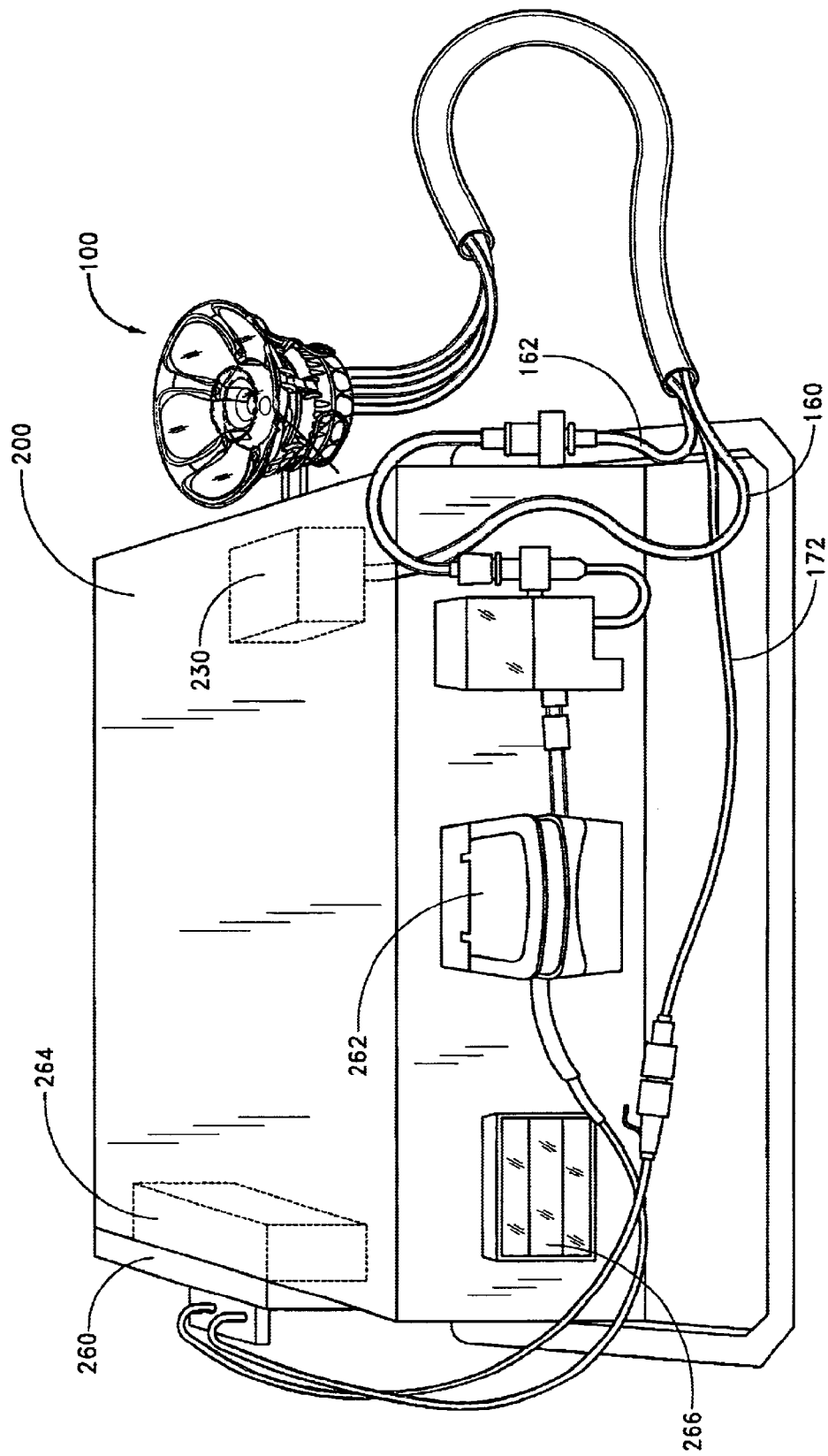
FIG. 12 is an illustration of one embodiment of a self-contained intraductal fluid aspiration device.

Referring to FIG. 12, a self-contained intraductal fluid aspiration device is depicted schematically illustrating the components. It should be apparent to one of skill in the art that the device may be a desk top unit, or alternatively stored on a movable cart, such that one device can be selectively utilized at various patient treatment locations. Although disclosed with only a single power head 100 for simplicity, the system may be provided with two power heads 100 for simultaneous operation. A control unit 200 houses the apparatuses for delivering heat, inflation media, and vacuum pressure, in addition to housing feedback and control devices 266 to allow an operator thereof to customize the operational characteristics, such as, for example, temperature, inflation pressure, inflation cycle characteristics, vacuum pressure, vacuum cycle characteristics, and the like. The control unit 200 houses a vacuum generator pump 230 for creating a vacuum pressure within at least the second concavity 166 of the power head 100 as previously described. The vacuum conduit 160 may be permanently attached to the power head 100, the vacuum generator pump 230, or may be removably attached to both. In this way, the vacuum conduit 160 may be replaced as desired.

The control unit 200 further contains a pump 262 for driving the compression cycle, and in one embodiment, the pump is a three or four-roller peristaltic pump. The pump 262 is preferably controlled by a control circuit, which includes instructions for controlling the pump 262 to deliver various modes of operation as described herein. The control circuit can also include instructions for operating the vacuum generating pump 230, and is configured to control the vacuum pressures created by the vacuum generating pump 230. The pump 262 is in compressive contact with at least a portion of one of the inflation conduits 162, and imparts a peristaltic pumping action thereto to force inflation media to flow through the inflation conduit 162. The pump 262 may also be reversible to deflate the inflatable bladders 204.

The inflation conduits 162, 172, meet at one end in a fluid reservoir 260 that contains a volume of inflation media. The fluid reservoir 260 may be a rigid tank, or may be a flexible bag, and may contain a volume within the range of from about 50 mL to one liter, and in some embodiments, may contain between about 150 mL and 300 mL, and in one embodiment, approximately 200 mL. The fluid reservoir 260 is adjacent to, and removably in thermal contact with, a heat exchanger 264 for conducting thermal energy into the inflation media. The heat exchanger 264 may be any of a number of known heaters, such as, for example, an electrical resistance heater. As described above, the inflation media is heated to a temperature within the range of about 30° C. to about 55° C., and more preferably within the range of from about 37° C. to about 50° C. To reduce the warm up time prior to use, a secondary, or even a tertiary heater may be installed.

The heated inflation media flows through an inflation conduit 172, and into the inflatable bladder 152 within the power head 100. The inflation media may be continuously cycled through the power head 100 and back to the fluid reservoir 260 for heating.

The inflation conduits 162, 172, inflatable bladder 152, and fluid reservoir 260 form a closed fluid loop, which is preferably removable from the system for periodic replacement. To install the fluid loop, the fluid reservoir 260 is inserted into a compartment housed in the control unit 200, and one of the inflation conduits 162, 172, is positioned across the pump 262. In this way, the closed fluid loop is isolated from the rest of the system and may easily be replaced, if necessary. It also keeps the inflation media separate from any electronics that are moisture sensitive. Hence, the closed fluid loop is not only convenient, but adds an element of safety to the apparatus, the operator, and the patient. To further protect the sensitive components in the control unit 200, bulkheads within the control unit 200 keep the electronics separate from the fluid loop.

Thus, according to one aspect of the present invention, a control unit contains circuitry and hardware for effecting the treatment methods disclosed herein. Specifically, a vacuum generator pump, fluid circulation pump, heat exchanger, and concomitant drivers are provided for carrying out an intraductal fluid aspiration procedure.

Some embodiments disclosed herein teach the use of a sample collector or reservoir positioned in fluid communication with the patient interface 154 to allow collection of intraductal fluid. In other embodiments, the aspirated fluid is allowed to collect on the tissue contacting surface 156 of the patient interface 154, with an amount of aspirated fluid likely to remain on the patient's skin, for subsequent cotton swab collection.

Additional embodiments may include a fluid detection device for alerting the operator when a fluid sample has been aspirated. The detection device may be in the form of a conductivity sensor in which the aspirated fluid bridges an electrical gap and completes an electrical circuit for actuating a visual or audible cue to alert an operator that a fluid sample has been collected. Alternatively, the fluid detection device may comprise a pH strip that will change color or otherwise alert an operator that a fluid sample has been collected.

To perform an intraductal fluid aspiration procedure, a technician prepares the patient by applying alcohol to remove keratin plugs. The technician determines the approximate size of breast to be tested, either visually, or through patient disclosure. The power head, with attached patient interface, may be rough adjusted to conform to the size and/or shape of the breast to be tested. Alternatively, the power head is fully opened to facilitate proper positioning around the nipple. Subsequent to contacting the patient, the power head is adjusted to properly fit the patient undergoing testing. Preferably, prior to contacting the patient, the inflation media has been preheated to a desired temperature and the pump idly delivers media flow through the power head. Once the power head is in contact with the patient and has been properly adjusted, the inflatable bladders receive additional inflation media and begin compressing the breast. A vacuum may be applied to at least the nipple to encourage fluid aspiration.

The procedure is anticipated to take approximately between 3 and 20 minutes to complete, and more preferably, is anticipated to take no more than approximately 10 minutes to complete. The procedure is complete upon either (1) collecting a sufficient volume of intraductal fluid, or (2) timing out of the procedure and determining that a sufficient fluid sample cannot be collected during this initiation of the procedure.

Upon procedure completion, the compression is halted and the inflatable bladder is deflated. Additionally, the vacuum is ceased and a vacuum releasing mechanism is actuated to remove the power head from the patient. In one embodiment where no sample collection patch is used, the fluid sample will collect on the inner surface of the patient interface, with a volume of fluid likely remaining on the patient for cotton swab collection. In the alternative, a fluid collection patch may be inserted into the patient interface such that it maintains contact with the nipple and collects the fluid sample by absorption.

Although the present inventors believe that sufficient sample volume will be obtainable from most patients using the heat, compression and suction cycles provided by the pump disclosed herein, some patients may benefit from administration of one or more agents to enhance productivity. For example, oxytocin may be administered, preferably via intranasal administration, in amounts effective to stimulate mammary fluid expression in the patient. Once a sufficient post-administration time period has elapsed to allow the oxytocin to reach and stimulate target alveolar-ductal tissues, the breast is pumped and a biological sample is collected, as described above. After the sample is collected, a bioassay is conducted on the sample to determine the presence and/or amount of a selected breast disease marker, preferably a breast cancer marker or panel of breast cancer markers, in the sample.

One additional manner of increasing the collected fluid volume is to introduce a carrier fluid retrograde into the duct, such as through the use of a pressurized stream directed to the external opening of the duct. The carrier may alternatively be introduced using an introduction needle or cannula which is advanced either transluminally through the duct or percutaneously. The carrier fluid may increase mobilization of cellular fragments and other markers, which will be available upon aspiration of the fluid for assay. Aspiration may occur either immediately following introduction of the carrier fluid, or after a sufficient indwelling period of time to permit mobilization of carrier soluble or carrier transportable cells, cell components, or markers.

Any of a wide variety of carriers may be utilized, depending upon the desired clinical objective. For example, an aqueous solution may be provided with any of a variety of drugs or other active agents to either treat the breast, or facilitate the release and/or transport of identifiable markers.

Thus, there is provided in accordance with the present invention a method of screening for breast cancer or other breast disease, comprising the steps of providing a patient having at least one breast duct with an external opening. A stream of carrier fluid is directed under pressure into the opening to introduce a volume of carrier fluid into the duct. The fluid is thereafter removed from the duct through the external opening, and the removed carrier fluid is screened for at least one indicium of a physiological condition such as a marker as discussed in greater detail elsewhere herein. The removing carrier fluid step is preferably accomplished by the application of suction to the external opening of the duct. Preferably, suction is accompanied by compression such as peristaltic or other systemic compression. The compression device is preferably heated, such as in accordance with the device discussed above. The screening step may be accomplished by screening for cytologically abnormal cells, or markers as discussed in detail elsewhere herein.

Another aspect of the method includes the introduction of a therapeutic species into a breast duct, with or without subsequent aspiration for marker assay. In accordance with this method, a media is provided, comprising a carrier and at least one therapeutic species. A stream of a media is directed at the external opening to the duct, to introduce media into the duct.

Any of a variety of devices may be utilized, to direct a pressurized fluid stream. See, for example, U.S. Pat. No. 5,399,163 to Peterson, et al., entitled "Needleless Hypodermic Injection Methods and Device," the disclosure of which is incorporated in its entirety herein by reference. Such devices are currently known in the arts of needleless injection and surgical pressurized water cutting devices, both of which may be modified to reduce the velocity of the fluid stream so that it is insufficient to cause tissue damage but sufficient to introduce carrier fluid retrograde into the duct. Introduction may be further facilitated by optimizing the viscosity and temperature of the fluid carrier, which may be accomplished through routine experimentation by those of ordinary skill in the art in view of the disclosure herein. Powered carrier introduction is preferably preceded by keratin plug removal, as discussed elsewhere herein.

As used herein, the term breast disease marker refers to any cell, cell fragment, protein, peptide, glycoprotein, lipid, glycolipid, proteolipid, or other molecular or biological material that is uniquely expressed (e.g. as a cell surface or secreted protein) by diseased breast cells, or is expressed at a statistically significant, measurably increased or decreased level by diseased breast cells, or in association with breast disease (e.g. a protein expressed by an infectious agent associated with breast disease), or is expressed at a statistically significant, measurably increased or decreased level by diseased breast cells compared to normal breast cells, or which is expressed by non-diseased breast cells in association with breast disease (e.g. in response to the presence of diseased breast cells or substances produced therefrom). Breast disease markers can also include specific DNA or RNA sequences marking a deleterious genetic change, or an alteration in patterns or levels of gene expression significantly associated with breast disease. Preferred breast disease markers include markers of breast infections, benign neoplasia, malignant neoplasia, pre-cancerous conditions, and conditions associated with an increased risk of cancer. Breast disease markers include breast cancer markers.

As used herein, the term breast cancer marker refers to a subset of breast disease markers, namely any protein, peptide, glycoprotein, lipid, glycolipid, proteolipid, or other molecular or biological material that is uniquely expressed (e.g. as a cell surface or secreted protein) by cancerous cells, or is expressed at a statistically significant, measurably increased or decreased level by cancerous cells compared to normal cells, or which is expressed by non-cancerous cells in association with cancer (e.g. in response to the presence of cancerous cells or substances produced therefrom). Breast cancer markers can also include specific DNA or RNA sequences marking a deleterious genetic change, or an alteration in patterns or levels of gene expression significantly associated with cancer. In addition, breast cancer markers can include cytological features of whole cells present in mammary fluid, such as nuclear inclusions or cytoplasmic structures or staining attributes uniquely expressed by, or associated with, cancerous cells.

Among the breast cancer markers that are useful within the methods of the invention, a subset are described in representative review articles by Porter-Jordan et al., Hematol. Oncol. Clin. North Amer. 8: 73–100, 1994; and Greiner, Pharmaceutical Tech, May, 1993, pp. 28–44, each incorporated herein by reference in its entirety. Other suitable markers are also widely known and can be readily incorporated into the methods of the invention using information and methods generally known or available in the literature. Preferred breast cancer markers for use within the invention include well characterized markers that have been shown to have important value for determining prognostic and/or treatment-related variables in human female patients. As noted previously, prognostic variables are those variables that serve to predict outcome of disease, such as the likelihood or timing of relapse or survival. Treatment-related variables predict the likelihood of success or failure of a given therapeutic program. Determining the presence or level of expression or activity of one or more of these markers can aid in the differential diagnosis of patients with malignant and benign abnormalities, and can be useful for predicting the risk of future relapse or the likelihood of response to a selected therapeutic option.

It is important to note, however, that the invention does not rely solely on breast disease markers that meet the stringent requirements of sensitivity and specificity that would render the marker immediately acceptable for clinical application to human patients. On the contrary, a number of breast disease markers contemplated within the invention fall short of these stringent criteria, and nonetheless provide useful information that can be of substantial benefit in detecting, differentially diagnosing or managing breast health including breast cancer. Such non-clinically accepted markers are useful for immediate application within the methods of the invention as basic research tools, and as adjunctive tools in clinical applications. Beyond these immediate applications, many such markers are expected to be further developed and refined according to the methods of the invention to the point of direct clinical applicability, particularly in assay methods that analyze combinations of markers to generate complementary data of greater predictive value than data yielded by individual markers alone.

The preferred assay methods of the invention particularly focus on breast cancer markers associated with tumorigenesis, tumor growth, neovascularization and cancer invasion, and which by virtue of this association provide important information concerning the risk, presence, status or future behavior of cancer in a patient. As noted previously, tumorigenesis and tumor growth can be assessed using a variety of cell proliferation markers (for example Ki67, cyclin D1 and PCNA). Tumor growth can also be evaluated using a variety of growth factor and hormone markers (for example estrogen, EGF, erbB-2, and TGF.alpha.), receptors of autocrine or exocrine growth factors and hormones (for example IGF and EGF receptors), or angiogenic factors. In addition to tumorigenic, proliferation and growth markers, a number of markers provide information concerning cancer invasion or metastatic potential in cancer cells, for example by indicating changes in the expression or activity of cell adhesion or motility factors. Exemplary markers in this context include Cathepsin D, plasminogen activators and collagenases. In addition, expression levels of several putative tumor "suppressor" genes, including nm23, p53 and rb, provide important data concerning metastatic potential, or growth regulation of cancer cells. Assays directed to divalent cations, such as $Ca^{2+}$, $Zn^{2+}$, and the like may also be helpful in providing important information concerning the risk, presence, status or future behavior of breast cancer. A large number and variety of suitable breast cancer markers in each of these classes have been identified, and many of these have been shown to have important value for determining prognostic and/or treatment-related variables relating to breast cancer.

Depending upon the chemistry of any particular assay, the results may be processed and expressed in a variety of ways. For example, for certain assays, a color change may be expressed directly from the sample collection patch in the pump. For other assays, the sample collection patch may be removed from the pump and developed in a desk top developing kit which includes whatever reagents, rinse solutions or other materials may be necessary to produce a result. For other assays, the sample collection patch is mailed or otherwise transported to a suitable laboratory for processing.

Prior to or concurrent with each assay run of the invention, particularly in the case of assays preformed at a remote laboratory, a preliminary evaluation may be performed to verify sample origin and/or quality. The focus of such preliminary evaluations is to verify that the sample collected in the collection patch is indeed of mammary origin, and is not contaminated with other potential contaminants, such as sweat from skin surrounding the nipple. For these sample verification purposes, a variety of assays are available which identify mammary fluid markers known to be present in mammalian mammary fluid, and which are preferably highly specific markers for mammary fluid (i.e. markers which are typically always present in mammary fluid and which are absent from all, or most of, other potentially contaminating bodily fluids and tissues).

However, an acceptable level of specificity for mammary fluid markers within the methods of the invention is provided by markers that are simply known to be present in mammary fluid, even though they may be present in other bodily fluids. One such marker is the enzyme lysozyme, which is a normal component of human serum, urine, saliva, tears, nasal secretions, vaginal secretions, seminal fluid, and mammary fluid. Lysozyme (muramidase) is an enzyme which hydrolyzes beta 1,4-glycosidic linkages in the mucopolysaccharide cell wall of a variety of microorganisms resulting in cell lysis. Quantitative measurement of lysozyme is readily accomplished by a well known agar plate diffusion method, described in detail in the instructions provided with the Quantiplate.RTM. lysozyme test kit, available from Kallestad, Sanofi Diagnostics (Chasta, Minn.), incorporated herein by reference in its entirety.

Other mammary fluid markers for sample verification that are more specific than lysozyme are preferred within the methods of the invention, and can be readily incorporated within the invention based on published and generally known information. The most preferred among these markers are proteins and other biological substances that are specifically expressed or enriched in mammary fluid. A diverse array of suitable markers in this context have been characterized and have already been used to develop specific antibodies, including affinity purified and monoclonal antibodies. These antibodies can in turn be employed as immunological probes to determine the presence or absence, and/or to quantify, selected mammary fluid markers to verify mammary fluid sample origin and quality.

Mammary fluid markers of particular interest for use within the invention include specific cytokeratins that are characteristically expressed by normal and cancerous mammary epithelial cells, against which specific panels of antibody probes have already been developed. (See for example, Nagle, J. Histochem. Cytochem. 34: 869–881, 1986, incorporated herein by reference in its entirety). Also useful as mammary fluid markers are the human mammary epithelial antigens (HME-Ags) corresponding to glycoprotein components of the human milk fat globulin (HMFG) protein, against which specific antibodies (e.g. anti HMFG1, Unipath, U.K.) are also available. (see Rosner et al., Cancer Invest. 13: 573–582, 1995; Ceriani et al. Proc. Natl. Acad. Sci. USA 74: 582–586, 1982; Ceriani et al., Breast Cancer Res. Treat. 15; 161–174, 1990, each incorporated herein by reference in its entirety).

To conduct the breast disease marker assays provided within the invention, a collected biological sample from mammary fluid is generally exposed to a probe that specifically binds to a selected breast disease or breast cancer marker, or otherwise interacts with the marker in a detectable manner to indicate the presence or absence, or amount, of the breast disease or breast cancer marker in the sample. Selected probes for this purpose will generally depend on the characteristics of the breast disease marker, i.e. on whether the marker is a protein polynucleotide or other substance. In preferred embodiments of the invention, the breast disease marker is a protein, peptide or glycoprotein, all of which are effectively targeted in breast disease marker assays using specific immunological probes. These immunological probes can be labeled with a covalently bound label to provide a signal for detecting the probe, or can be indirectly labeled, for example by a labeled secondary antibody that binds the immunological probe to provide a detectable signal.

General methods for the production of non-human antisera or monoclonal antibodies (e.g., murine, lagormorpha, porcine, equine) are well known and may be accomplished by, for example, immunizing an animal with a selected breast disease marker protein, peptides synthesized to include part of the marker protein sequence, degradation products including part of the marker protein sequence, or fusion proteins including all or part of the marker protein linked to a heterologous protein or peptide. Within various embodiments, monoclonal antibody producing cells are obtained from immunized animals, immortalized and screened, or screened first for the production of an antibody that binds to the selected breast cancer marker protein or peptide, and then immortalized.

It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397 (incorporated herein by reference in its entirety). Alternatively, a human monoclonal antibody or portions thereof may be identified by first screening a human B-cell cDNA library for DNA molecules that encode antibodies that specifically bind to the selected breast disease marker according to the method generally set forth by Huse et al. (Science 246: 1275–1281, 1989 (incorporated herein by reference in its entirety). The DNA molecule may then be cloned and amplified to obtain sequences that encode the antibody (or binding domain) of the desired specificity.

Also contemplated within the invention are bifunctional antibodies having independent antigen binding sites on each immunoglobulin molecule (as disclosed for example in Thromb. Res. Suppl. X: 83, 1990, and in The Second Annual IBC International Conference on Antibody Engineering, A. George ed., Dec. 16–18, 1991; each incorporated herein by reference in its entirety), as well as panels of individual antibodies having differing specificities. Bifunctional antibodies and antibody panels of particular use within the invention include antibodies and panels of antibodies that bind to two or more selected breast disease markers to generate complementary data of greater predictive value than data yielded by individual markers alone.

Monoclonal antibodies are particularly useful within the invention as labeled probes to detect, image and/or quantify the presence or activity of selected breast disease markers. In this context, monoclonal antibodies that specifically bind to selected breast disease markers are provided which incorporate one or more well known labels, such as a dye, fluorescent tag or radiolabel. By incorporating such a label, the antibodies can be employed in routine assays to determine expression, localization and/or activity of one or more selected breast disease markers in a biological sample including, or derived from, mammary fluid.

Results of these assays to determine expression, localization and/or activity of a selected breast disease marker in a test sample taken from a patient at risk for breast disease, or known to have breast disease, can be compared to results from control studies detecting and/or quantifying the same marker in biological samples obtained from normal patients negative for breast disease. In this manner, baseline data and cutoff values can be determined according to routine methods to refine the assays of the invention and adapt them for direct clinical application.

Detection and/or quantification of breast disease markers in the biological samples of the invention can be accomplished using a variety of methods. Preferred methods in this regard include well known ELISA immunoassays, immunoprecipitation assays, and various solid phase immunoassays including Western blotting, dot blotting and affinity purification immunoassays, among other methods. Comparable methods are disclosed herein, or are elsewhere disclosed and known in the art, for using non-antibody probes to detect and/or quantify the expression and/or activity of breast disease markers. Suitable non-antibody probes for use within the invention include, for example, labeled nucleotide probes that hybridize at standard or high stringency to DNA transcripts of oncogenes and other DNA sequences associated with elevated breast disease risk, or with mRNA transcripts encoding breast disease marker proteins. Other suitable probes include labeled ligands, binding partners and co-factors of breast disease markers (e.g. growth factor receptor ligands, or substrates of breast cancer associated proteases such as Cathepsin D).

In certain embodiments of the invention, cDNA and oligonucleotide probes are employed in Northern, Southern and dot-blot assays for identifying and quantifying the level of expression of a selected breast disease marker in cell samples collected from expressed mammary fluid. Measuring the level of expression of breast disease markers according to these methods will provide important prognostic and treatment-related information for assessing a broad range of breast disease, including the genesis, growth and invasiveness of cancer, in mammals, particularly humans. For example, assays utilizing oligonucleotide probes will assist early screening to evaluate heritable genetic lesions associated with breast cancer, and to distinguish between pre-cancerous, early cancerous and likely metastatic lesions in patients.

In addition to the above mentioned sample extraction, collection and assay methods, the invention also provides kits and multicontainer units comprising reagents and components for practicing the sample collection and assay methods of the invention. Briefly, these kits include basic components for obtaining a biological sample from mammary fluid.

A pharmaceutical preparation of oxytocin in a biologically suitable carrier may optionally be included. Preferably, the oxytocin preparation is provided in an intranasal spray applicator and contains approximately 40 USP units of oxytocin per ml of liquid carrier, which carrier is a simple, inexpensive buffered saline solution. Preferred applicators can be in any of a variety of pressurized aerosol or hand-pump reservoir forms, with a nozzle for directing a liquid spray of the oxytocin into a patient's nostril.

The breast pump of the present invention is also provided. The pump is designed to generate intermittent or sustained negative pressures in an area surrounding the nipple of between about 50–200 mmHg, as well as heat and compression as has been discussed. Preferably, the breast pump serves a dual purpose of facilitating mammary fluid expression from the nipple, and to provide the reservoir or solid phase collecting device incorporated within the breast pump for biological sample collection.

Kits for practicing the assay methods of the invention include a suitable container or patch or other device for collecting a biological sample from expressed mammary fluid. A range of suitable collection devices are contemplated corresponding to a wide range of suitable biological samples that may be collected from the expressed mammary fluid. For example, simple sterile containers or reservoirs are provided to collect whole mammary fluid. Alternatively, a variety of solid phase devices, including glass or plastic slides, membranes, filters, beads and like media, are provided to receive or partition selected liquid or solid fractions of the mammary fluid, to receive or partition cells or cellular constituents from the mammary fluid, or to receive or partition purified or bulk proteins, glycoproteins, peptides, nucleotides (including DNA and RNA polynucleotides) or other like biochemical and molecular constituents from the mammary fluid. A wide variety of such sample collection devices can be readily adapted for use within specific embodiments of the invention. These collection devices may be provided as a component of the breast pump (such as a removable fluid reservoir or nitrocellulose filter placed within the pump to directly receive or contact the expressed mammary fluid as it is pumped), or may be provided separately (for example as a non-integral membrane, filter, affinity column or blotting material to which mammary fluid or mammary fluid components are exposed to collect a biological sample for assay purposes).

Although the foregoing invention has been described in terms of certain preferred embodiments, other embodiments and applications will become apparent to those of ordinary skill in the art in view of the disclosure herein. Accordingly, the present invention is not intended to be limited by the recitation of preferred embodiments, but is intended to be defined solely by reference to the appended claims.

What is claimed is:

1. A disposable patient interface for an intraductal fluid aspiration device, comprising:
    a flexible, unsupported, size-adjustable tubular membrane, adapted for removable attachment to a size-adjustable support, the tubular membrane having a proximal end, a distal end and a passageway extending therethrough, wherein the proximal end has a smaller cross sectional area than the distal end;
    a rigid proximal cap on the proximal end of the flexible tubular membrane; and
    a vacuum port on the cap for connection to a source of vacuum.

2. A disposable patient interface as in claim 1, wherein an unstressed diameter of the distal end is within the range of from about 2 inches to about 4 inches.

3. A disposable patient interface as in claim 1, wherein an unstressed diameter of the distal end is no mare than about 4 inches.

4. A disposable patient interface as in claim 1, wherein the diameter of the distal end is adapted to be stretched to at least 150% of its unstressed diameter without rupturing the membrane.

5. A disposable patient interface as in claim 1, wherein the diameter of the distal end is adapted to be stretched to at least 200% of its unstressed diameter without rupturing the membrane.

6. A disposable patient interface as in claim 1, wherein the axial length of the tubular membrane from a distal end of the proximal cap to the distal end of the tubular membrane, along the surface of the membrane, is within the range of from about 1 inch to about 6 inches.

7. A disposable patient interface as in claim 1, wherein the axial length of the tubular membrane from a distal end of the proximal cap to the distal end of the tubular membrane, along the surface of the membrane, is within the range of from about 2 inches to about 4 inches.

8. A disposable patient interface as in claim 1, wherein the proximal cap defines a chamber therein.

9. A disposable patient interface as in claim 8, wherein the proximal cap exhibits sufficient rigidity that the proximal cap resists collapse when a vacuum of at least about 150 mm Hg is applied to the chamber.

10. A disposable patient interface as in claim 9, wherein the proximal cap exhibits sufficient rigidity that the proximal caps resists collapse when a vacuum of at least about 250 mm Hg is applied to the chamber.

11. A disposable patient interface as in claim 1, wherein the proximal cap comprises at least a first retention structure for releasable connection with a complementary second retention structure on a handpiece.

12. A disposable patient interface as in claim 11, wherein the first retention structure comprises a recess on the proximal cap.

13. A disposable patient interface as in claim 11, wherein the first retention structure comprises a projection on the proximal cap.

14. A disposable patient interface as in claim 1, wherein the tubular membrane comprises a styrene block copolymer.

15. A disposable patient interface as in claim 1, wherein the tubular membrane has a wall thickness of no more than about 0.025 inches.

16. A disposable patient interface as in claim 1, wherein the tubular membrane has a wall thickness of no more than about 0.0125 inches.

17. A method of making a disposable patient interface for an intraductal fluid aspiration device, comprising the steps of:
    molding a proximal cap; and
    overmolding a flexible tubular membrane such that a substantial portion of the tubular membrane extends unsupported beyond the proximal cap.

* * * * *